US012661004B2

(12) United States Patent
Leung et al.

(10) Patent No.: US 12,661,004 B2
(45) Date of Patent: Jun. 23, 2026

(54) METHOD AND SYSTEM FOR DETERMINING RISK OF PRIMARY ANGLE CLOSURE AND RELATED GLAUCOMA FROM 360° IMAGING OF ANTERIOR CHAMBER ANGLES

(71) Applicant: The University of Hong Kong, Hong Kong (CN)

(72) Inventors: Kai-Shun Christopher Leung, Hong Kong (CN); Ka-Ngai Alexander Lam, Hong Kong (CN); Yawen Philip Guo, Hong Kong (CN)

(73) Assignee: The University of Hong Kong, Hong Kong (CN)

( * ) Notice: Subject to any disclaimer, the term of this patent is extended or adjusted under 35 U.S.C. 154(b) by 368 days.

(21) Appl. No.: 18/456,026

(22) Filed: Aug. 25, 2023

(65) Prior Publication Data

US 2024/0074657 A1    Mar. 7, 2024

Related U.S. Application Data

(60) Provisional application No. 63/373,607, filed on Aug. 26, 2022.

(51) Int. Cl.
*G06T 7/00* (2017.01)
*A61B 3/00* (2006.01)
(Continued)

(52) U.S. Cl.
CPC ............ *A61B 3/117* (2013.01); *A61B 3/0025* (2013.01); *A61B 3/102* (2013.01); *A61B 5/7267* (2013.01);
(Continued)

(58) Field of Classification Search
CPC ....... A61B 3/117; A61B 3/0025; A61B 3/102; A61B 5/7267; A61B 5/7275;
(Continued)

(56) References Cited

U.S. PATENT DOCUMENTS

2021/0386285 A1* 12/2021 Walsh ...................... A61B 3/18
2022/0361752 A1* 11/2022 Dirghangi .............. A61B 3/132
(Continued)

OTHER PUBLICATIONS

"European Glaucoma Society Terminology and Guidelines for Glaucoma, 4th Edition—Chapter 2: Classification and terminology Supported by the EGS Foundation: Part 1: Foreword; Introduction; Glossary; Chapter 2 Classification and Terminology," Br J Ophthalmo., 2017, 101:73-127.
(Continued)

*Primary Examiner* — Iriana Cruz
(74) *Attorney, Agent, or Firm* — SALIWANCHIK, LLOYD & EISENSCHENK

(57) ABSTRACT

The subject invention pertains to a novel angle-closure detection method for risk assessment of primary angle closure (PAC) or primary angle closure glaucoma (PACG) to inform treatment decisions. According to certain embodiments, a plurality of cross-sectional images of the anterior segment of an eye centered at the pupil with preferably even radial separations are obtained from optical coherence tomography imaging. After identifying the position of scleral spur from the cross-sectional image captured at each angle-location, the anterior chamber angles are analyzed. Each angle-location of the eye is classified as (i) closed angle, (ii) narrow angle, or (iii) open angle. The extents of narrow angles and closed angles among all angle-locations across the 360° radial space are computed. Based on the extents of narrow angles and closed angles, a regression model is applied to compute the risk of PAC/PACG development.

18 Claims, 18 Drawing Sheets

(51) Int. Cl.
      *A61B 3/10*       (2006.01)
      *A61B 3/117*      (2006.01)
      *A61B 5/00*       (2006.01)
      *G06T 7/174*      (2017.01)
      *G16H 50/30*      (2018.01)
(52) U.S. Cl.
      CPC .......... *A61B 5/7275* (2013.01); *G06T 7/0014*
            (2013.01); *G06T 7/174* (2017.01); *G16H*
            *50/30* (2018.01); *G06T 2207/10101* (2013.01);
                  *G06T 2207/20021* (2013.01); *G06T*
            *2207/20076* (2013.01); *G06T 2207/20084*
            (2013.01); *G06T 2207/30041* (2013.01)
(58) Field of Classification Search
      CPC ................... G06T 7/0014; G06T 7/174; G06T
                  2207/10101; G06T 2207/20021; G06T
                  2207/20076; G06T 2207/20084; G06T
                  2207/30041; G06T 2207/20081; G06T
                                    7/11; G16H 50/30
      See application file for complete search history.

(56)                References Cited

U.S. PATENT DOCUMENTS

2023/0240526 A1*   8/2023  Li ........................... A61B 3/117
                                                      351/206
2023/0351073 A1*  11/2023  Hipsley ................... G06F 30/23
2024/0008811 A1*   1/2024  Sassu ....................... A61B 3/16

OTHER PUBLICATIONS

"Primary Angle Closure Preferred Practice Pattern," American Academy of Ophthalmology Glaucoma, Preferred Practice Pattern Panel, 2015, pp. 1-40, Elsevier Inc.
"Asia Pacific Glaucoma Guidelines. Amsterdam: Asian Pacific Glaucoma Society," Asian Pacific Glaucoma Society, 2016, pp. 1-156, Kugler Publications.
Aung, T., et al., "Configuration of the Drainage Angle, Intraocular Pressure, and Optic Disc Cupping in Subjects with Chronic Angle-Closure Glaucoma," Ophthalmology, 2005, 112:28-32, Elsevier, Inc.
Cohen, J.F., et al., "Stard 2015 guidelines for reporting diagnostic accuracy studies: explanation and elaboration," BMJ Open, 2016, 6:1-17.
Xu, B.Y., et al., "Ocular Biometric Risk Factors for Progression of Primary Angle Closure Disease," Ophthalmology, 2022, 129:267-275, Elsevier Inc.
Seager, F.E., et al., "The Effect of Scleral Spur Identification Methods on Structural Measurements by Anterior Segment Optical Coherence Tomography," J Glaucoma, Jan. 2014, 23(1):e29-e38.
Liu, S., et al., "Assessment of Sclera Spur Visibility with Anterior Segment Optical Coherence Tomography," J Glaucoma, Feb. 2010, 19(2):132-135.
Leung, C.K.-S., et al., "Anterior chamber angle imaging with optical coherence tomography," Eye, 2011, 25:261-267, Macmillan Publishes Ltd.
Liu, S., et al., "Anterior Chamber Angle Imaging with Swept-Source Optical Coherence Tomography: An Investigation on Variability of Angle Measurement," Investigative Ophthalmology & Visual Science, Nov. 2011, 52(12):8598-8603.
Romkens, H.C.S., et al., "Reproducibility of Anterior Chamber Angle Analyses With the Swept-Source Optical Coherence Tomography in Young, Healthy Caucasians," Investigative Ophthalmology & Visual Science, Jun. 2014, 55(6):3999-4004.

Chan, P.P-M., et al., "Anterior chamber angle imagine with swept-source optical coherence tomography: comparson between CASIAII and Anterion," Scientific Reports, 2020, 10(18771):1-8.
Choi, W., et al., "Comparison of the trabecular meshwork length between open and closed angle with evaluation of the scleral spur location," Scientific Reports, 2019, 9(6857):1-8.
Mori, S., et al., "Correlation Structures of Correlated Binomial Models and Implied Default Distribution," Journal of the Physical Society of Japan, Nov. 2008, 77(11):1-7.
Nolan, W.P., et al., "Detection of Primary Angle Closure Using Anterior Segment Optical Coherence Tomography in Asian Eyes," Ophthalmology, Jan. 2007, 114(1):33-39, Elsevier Inc.
Lavanya, R., et al., "Screening for Narrow Angles in the Singapore Population: Evaluation of New Noncontact Screening Methods," Ophthalmology, Oct. 2008, 115(10):1720-1727.
Porporato, N., et al., "Assessment of Circumferential Angle Closure with Swept-Source Optical Coherence Tomography: a Community Based Study," American Journal of Ophthalmology, Mar. 2019, 199:133-139, Elsevier Inc.
Porporato, N., et al., "Understanding diagnostic disagreement in angle closure assessment between anterior segment optical coherence tomography and gonioscopy," Br J Ophthalmol, 2020, 104:795-799.
Zhang, Y., et al., "Progression of Primary Angle Closure Suspect to Primary Angle Closure and Associated Risk Factors: The Handan Eye Study," Invest Ophthalmol Vis Sci., Jun. 2021, 62(7):1-8.
Thomas, R., et al., "Five year risk of progression of primary anle closure suspects to primary angle closure: a population based study," Br J Ophthalmol, 2003, 87:1-6.
Liza-Sharmini, A.T., et al., "Clinical Presentation, Severity and Progression of Primary Angle Closure in Malay and Chinese Patients," Med J Malaysia, Dec. 2014, 69(6):245-251.
Gupta, B., et al., "Quantification of Iridotrabecular Contact in Primary Angle-Closure Disease," J Glaucoma, Aug. 2020, 29(8):681-688.
He, M., et al., "Laser peripheral iridotomy for the prevention of angle closure: a single-centre, randomised controlled trial," Lancet, Apr. 20, 2019, 393:1609-1618.
Leung, C.K.-S., et al., "Dynamic Analysis of Dark-Light Changes of the Anterior Chamber Angle with Anterior Segment OCT," Investigative Ophthalmology & Visual Science, Sep. 2007, 48(9):4116-4122.
Quigley, H.A., et al., "The number of people with glaucoma worldwide in 2010 and 2020," Br J Ophthalmol, 2006, 90:262-267.
Liu, P., et al., "Reproducibility of deep learning based scleral spur localisation and anterior chamber angle measurements from anterior segment optical coherence tomography images," Br J Ophthalmol, 2022, 0:1-7.
Xu, B.Y., et al., "Deep Neural Network for Scleral Spur Detection in Anterior Segment OCT Images: The Chinese American Eye Study," Translational vision science & technology, 2009, 9(2):1-10.
Porporato, N., et al., "Towards 'automated gonioscopy': a deep learning algorithm for 360 degree angle assessment by swept-source optical coherence tomography," Br J Ophthalmol, 2022, 106:1387-1392.
Narayanaswamy, A., et al., "Diagnostic Performance of Anterior Chamber Angle Measurements for Detecting Eyes With Narrow Angles," Arch Ophthalmol., Oct. 2010, 128(10):1321-1327.
Melese, E.K., et al., "Determination and Validation of Thresholds of Anterior Chamber Parameters by Dedicated Anterior Segment Optical Coherence Tomography," American Journal of Ophthalmology, Sep. 2016, 169:208-217.
Zhang, X., et al., "Assessment of Iris Trabecular Contact in Eyes with Gonioscopic Angle-Closure," Ophthalmology, Jan. 2023, 130(1):111-119, Elsevier Inc.

* cited by examiner

Acquire cross-sectional scan images of the anterior segment of the patient's eye with evenly spaced circumferential separation across the 360° radial space using AS-OCT

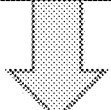

Locate scleral spur (SS) position on cross-sectional OCT image acquired at each scanned angle-location

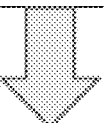

Measure anterior chamber angle (ACA) parameters for each angle-location based on the scleral spur position of the respective angle-location

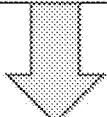

Determine whether the anterior chamber angle of each angle-location is abnormal (e.g. narrow/closed angle) based on the measured values of ACA parameters

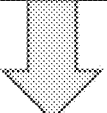

Calculate the extent of ACA abnormalities among all angle-locations

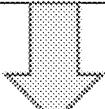

Determine the risk of disease development for the eye from a regression model based on the extent of ACA abnormalities found in the eye

FIG. 1

Grey sector: closed angle or narrow angle

Grey triangle: 5$^{th}$ percentile of the normative AOD500 distribution as cut-off values at each angle-location Square: measured AOD500 of this eye Grey sector: closed angle or narrow angle Grey triangle/cross/ star: 5<sup>th</sup>/median/95<sup>th</sup> percentile of the normative AOD500 distribution at each angle-location Square: measured AOD500 of this eye

METHOD AND SYSTEM FOR DETERMINING RISK OF PRIMARY ANGLE CLOSURE AND RELATED GLAUCOMA FROM 360° IMAGING OF ANTERIOR CHAMBER ANGLES

CROSS-REFERENCE TO RELATED APPLICATION

The present application claims the benefit of U.S. Provisional Application Ser. No. 63/373,607, filed Aug. 26, 2022, which is hereby incorporated by reference herein in its entirety, including any figures, tables, or drawings.

BACKGROUND OF INVENTION

Current standard for diagnosis of angle-closure in eyes is largely predicated on gonioscopy assessment. However, reported rates of disease progression from gonioscopic angle closure to primary angle closure (PAC) or primary angle closure glaucoma (PACG) vary widely due to its low precision in detection of iris trabecular contact (ITC). There is an unmet need to develop a more relevant angle-closure detection method for risk assessment of PAC/PACG to inform treatment decisions.

Closure of anterior chamber angle (ACA), or angle closure, of the eye is one of the main causes for glaucoma, an irreversible blindness affecting millions of patients worldwide. Whereas the presence of iris trabecular contact (ITC) is indicative of angle closure, clinical diagnosis of angle closure in primary angle closure disease (PACD), including primary angle closure suspect (PACS), primary angle closure (PAC), and primary angle closure glaucoma (PACG) is contingent on dark room gonioscopy when the posterior trabecular meshwork is not visible for at least 180°.

Non-visible posterior trabecular meshwork, however, does not always denote ITC. Discerning ITC is difficult on gonioscopy because clinical judgement of the apposition between the peripheral iris and the trabecular meshwork is always subject to the influence of slit-lamp illumination. Like slit-lamp illumination, inadvertent corneal indentation during gonioscopy can also widen the ACA and obscures the observation of ITC. Anatomic variations in the anterior segment and ACA configurations can also contribute to the diagnostic disagreement. Eyes with ITC but with a deep anterior chamber depth (CAD) and low lens vault can give an impression of open angle on gonioscopy whereas eyes with gonioscopic angle closure having a steep iris configuration can have no ITC.

The importance of discriminating a closed angle (i.e., with ITC) from a narrow angle (i.e., without ITC) stems from the fact that eyes with ITC would likely pose additional risks of development of peripheral anterior synechiae (PAS), elevation of intraocular pressure (IOP), and subsequently progression to PACG. Being able to optically dissect the ACA in cross-section in the dark, the anterior segment-optical coherence tomography (AS-OCT) is more precise than gonioscopy to reveal the presence and the extent of ITC.

It is therefore desirable to provide improved methods and systems other than gonioscopy assessment for better risk assessment of PAC/PACG and informing treatment decisions.

BRIEF SUMMARY

Embodiments of the subject invention relate to a system, method, or apparatus for providing a computerized method for determining the risk of disease progression in an eye based on 360° imaging of anterior chamber angle. In certain embodiments, a plurality of cross-sectional images of the anterior segment of an eye centered at the pupil with preferably, but not necessarily, evenly spaced radial separations are obtained from optical coherence tomography (OCT) imaging. After identifying the position of scleral spur (SS) and segmenting the boundaries of the cornea and iris from the cross-sectional image captured at each angle-location, the anterior chamber angles (ACA) are analyzed. The values of ACA parameters such as angle opening distance (AOD) and trabecular iris space area (TISA) are determined for each angle-location based on the identified SS position and segmented cornea and iris boundaries. Each angle-location of the eye is classified as (i) closed angle if the ACA parameter value is equal to zero, (ii) narrow angle if the ACA parameter value is below a specific cutoff-percentile when compared with the normative distribution at the corresponding angle-location, or (iii) open angle if the ACA parameter value is above or equal to the cutoff-percentile. The extents of narrow angles and closed angles among all angle-locations across the 360° radial space are computed. Based on the extents of narrow angles and closed angles, a regression model is applied to compute the risk of PAC/PACG development.

Certain embodiments relate to methods, apparatuses, and computer-readable media for detecting abnormalities in the anterior chamber angles or other characteristics in the anterior segment of an eye to assess the risk of PAC/PACG development using AS-OCT imaging.

Some embodiments include receiving a plurality of cross-sectional scan images of the anterior segment of the patient's eye, wherein the plurality of images is acquired in evenly spaced circumferential separations with reference to the central axis of pupil in one complete scan at a time, forming 360° imaging of the anterior segment. The position of the SS is then identified from the cross-sectional image at each of the scanned angle-locations. In some embodiments, the SS position is detected automatically using a deep neural network model trained with deep learning.

A set of anterior chamber angle (ACA) parameters are measured from the cross-sectional image at each respective angle-location based on the identified SS position. A respective value for each of the ACA parameters of the respective angle-location can be determined (e.g., measurements of AOD or TISA). For each of the scanned angle-locations, it is then determined whether the respective ACA values that correspond to the respective angle-location exhibit abnormality in the patient's eye, and the respective ACA is classified as (i) closed angle if the ACA value is equal to zero, (ii) narrow angle if the ACA value is below a respective threshold ACA value for the respective angle-location, or (iii) open angle if the ACA value is above or equal to a respective threshold ACA value for the respective angle-location. In some embodiments, the threshold ACA value of an angle-location is determined from a specific cut-off percentile of the age-related distribution of that particular angle-location. The age-related distribution can be determined from a cross-sectional dataset collected from a normal healthy cohort. In some embodiments, the k-th percentile used to determine the threshold ACA value at one angle-location is not necessarily the same as the other angle-locations.

The extents of narrow angles and closed angles among all angle-locations across 360° are computed. Based on the extents of narrow angles, closed angles, or a combination of both, a regression model is applied to compute the risk of PAC/PACG development. Once the risk of PAC/PACG development has been identified, a disease prognosis and a treatment plan can be provided.

Other embodiments include dividing the scanned angle-locations of the eye into a plurality of angle-location partitions, where each angle-location partition includes one or more adjacent angle-locations. By way of exemplary and non-limiting example, the 360° radial space can be divided into one of the following: 2 partitions of angle-locations with each partition covering 180°; 4 partitions of angle-locations with each partition covering 90°; 6 partitions of angle-locations with each partition covering 60°; or each partition can include a predetermined number of angle-locations or a predetermined portion of the 360° radial space. A partition can be determined as abnormal based on the extents of narrow and/or closed angles among that particular partition. A regression model for each angle-location partition set can then be calculated from the respective abnormalities of the angle-location partitions, with a computer system. The regression model can generate a value reflecting the risk of PAC/PACG development.

Embodiments are also directed to systems and computer-readable media associated with methods described herein. The following detailed description, together with the accompanying drawings and figures, will provide a better understanding of the nature and advantages of the subject invention. The features described herein are not all-inclusive and many additional features will be apparent to one of ordinary skill in the art in view of figures and description. Moreover, it should be noted that the language used in the specification has been principally selected for readability and instructional purposes and not to limit the scope of the inventive subject matter.

BRIEF DESCRIPTION OF DRAWINGS

FIG. 1 illustrates an analysis workflow in accordance with an embodiment of the subject invention.

As seen in FIG. 4A, the AOD250 is defined and measured as the perpendicular distance from the posterior corneoscleral junction at 250 μm anterior to the SS to the anterior iris surface. TISA250 represented the area bounded anteriorly by the AOD250, posteriorly by a line drawn from the SS perpendicular to the plane of the inner scleral wall to the opposing iris, superiorly by the inner corneoscleral wall, and inferiorly by the anterior iris surface. As seen in FIG. 4B, the AOD500 is defined and measured as the perpendicular distance from the posterior corneoscleral junction at 500 μm anterior to the SS to the anterior iris surface. TISA500 represented the area bounded anteriorly by the AOD500, posteriorly by a line drawn from the SS perpendicular to the plane of the inner scleral wall to the opposing iris, superiorly by the inner corneoscleral wall, and inferiorly by the anterior iris surface.

DETAILED DISCLOSURE

Figure 2:
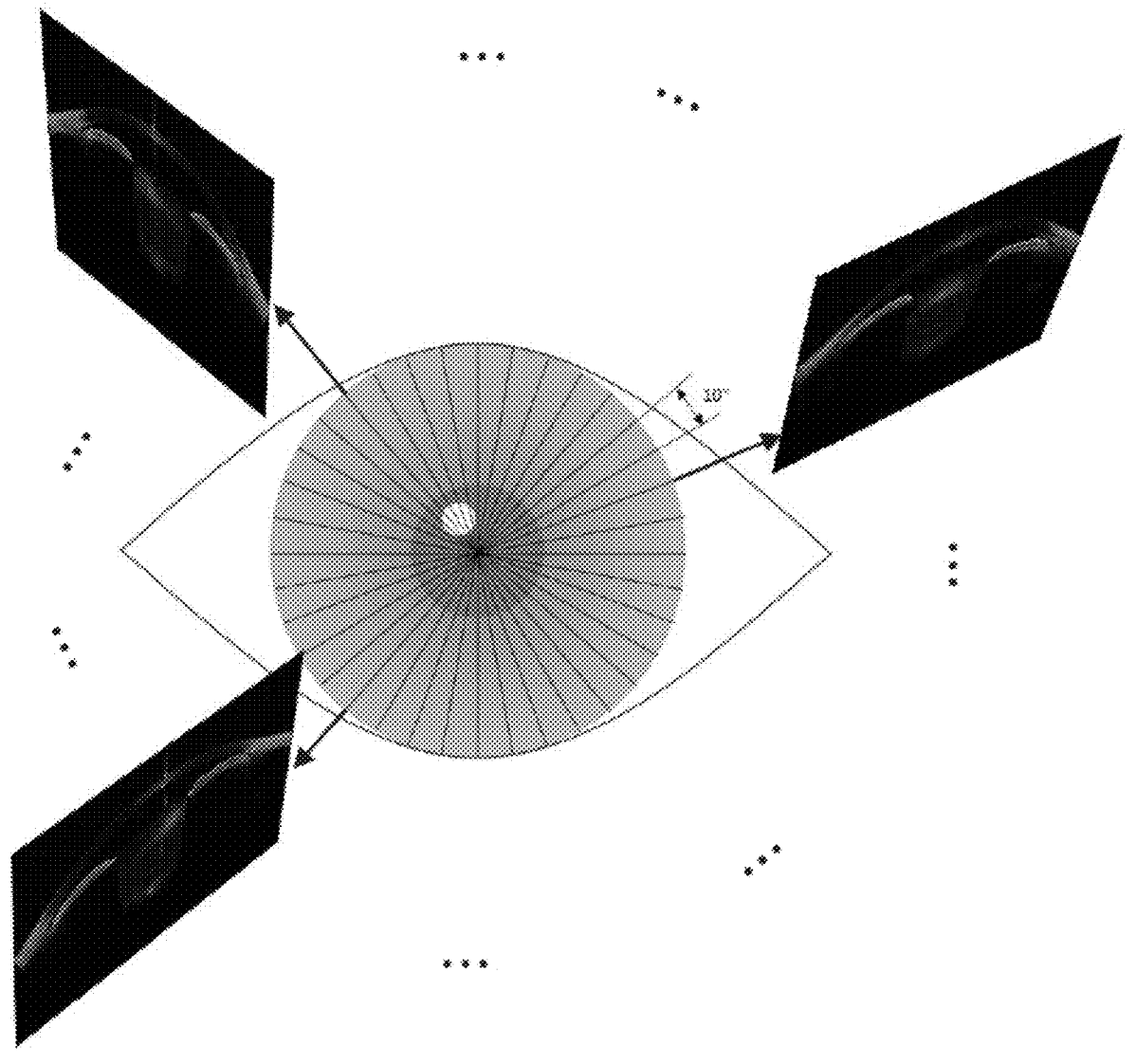
FIG. 2 illustrates an example scan protocol of 360° imaging of the anterior segment of an eye with 36 cross-sectional scans obtained from 36 angle-locations, with evenly spaced circumferential separations with reference to the central axis of the pupil (i.e., at the center of the eye, where the circumferential separations intersect in the illustration) and each angle-location spanning approximately 100 in accordance with an embodiment of the subject invention.

Embodiments of the subject invention provide techniques to determine the risk of disease development based on circumferential anterior chamber angle (ACA) measurements, measured from 360° cross-sectional imaging of the anterior segment of a patient's eye. ACA measurements in the patient's eye, if lower than corresponding angle-location-specific age-related thresholds or equal to zero, can signal eye abnormalities, such as primary angle closure (PAC) or primary angle closure glaucoma (PACG).

Current standard for detecting ACA closure using gonioscopy assessment to examine for presence of iris trabecular contact (ITC) can be limited. Discerning ITC is difficult on gonioscopy due to limitations residing on the fundamental principles of the examination technique. For example, inevitable slit-lamp illumination and inadvertent corneal indentation during gonioscopy can obscure the detection of ITC. Clinical judgement of the apposition between the peripheral iris and the trabecular meshwork can be subject to the influence of slit-lamp illumination. Like slit-lamp illumination, inadvertent corneal indentation can also widen the ACA and obscure ITC. In other words, non-visible posterior trabecular meshwork can occur in the absence of ITC. Besides, anatomic variations in the anterior segment and ACA configurations can also contribute to diagnostic disagreement. Eyes with ITC but with a deep anterior chamber depth (CAD) and low lens vault can give an impression of open angle on gonioscopy whereas eyes with gonioscopic angle closure having a steep iris configuration can have no ITC. ACD is an established anterior segment biometric parameter. Anatomically, it represents the distance between the corneal endothelium and the anterior capsule of the crystalline lens.

The conventional understanding of disease progression from PACS to PAC/PACG has been largely derived from eyes examined with gonioscopy and the reported rates of disease progression from PACS to PAC/PACG or acute angle closure (AAC) vary widely. In the Zhongshan Angle Closure Prevention Trial, 5.3% of 643 eyes with PACS progressed to PAC or AAC in 6 years (Xu B Y, et. al. Ocular Biometric Risk Factors for Progression of Primary Angle Closure Disease: The Zhongshan Angle Closure Prevention Trial. Ophthalmology. 2021:50161-6420(21)00746-6). In a recent population study, Zhang et al showed 6.08% of 526 patients with PACS progressed to PAC/PACG in 5 years (Zhang Y, et. al. Progression of Primary Angle Closure Suspect to Primary Angle Closure and Associated Risk Factors: The Handan Eye Study. Invest Ophthalmol Vis Sci. 2021; 62:2). By contrast, Thomas et al. reported that 22.0% of 50 PACS patients converted to PAC over 5 years (Thomas R, et. al. Five year risk of progression of primary angle closure suspects to primary angle closure: a population based study. Br J Ophthalmol. 2003; 87:450-4) and Lisa-Sharmini et al reported 56.0% of 112 eyes with PACS progressed to PAC/PACG over 5 years. (Liza-Sharmini A T, et. al. Clinical presentation, severity and progression of primary angle closure in malays. Med J Malaysia. 2014; 69:21-6.) The variable rates of disease progression can be partly attributed to the inter-study and inter-observer variability in gonioscopy assessment, and partly attributed to the varying extent of ITC in eyes with PACS, which could not be precisely measured with gonioscopy. Gonioscopy can in some cases fail to attain the required precision to determine the presence and the extent of ITC. Therefore, laser iridotomy is not recommended for all eyes with PACS and the risk of development of PAC/PACG or AAC likely varies widely in eyes with PACS because of the differential extent of ITC in individual eyes. Irreversible loss of vision could occur in patients with glaucoma if treatment is not provided at the early stage of disease when angle closure is detected. On the other hand, patients can be over-treated if the results of gonioscopy assessment are false positives.

Embodiments of the subject invention can solve these and other problems with 360° assessment of ITC with AS-OCT, including determining the risk of progression from PACS to PAC/PACG and informing the treatment decision. The workflow of an embodiment of the subject invention is illustrated in FIG. 1.

Figure 3A:
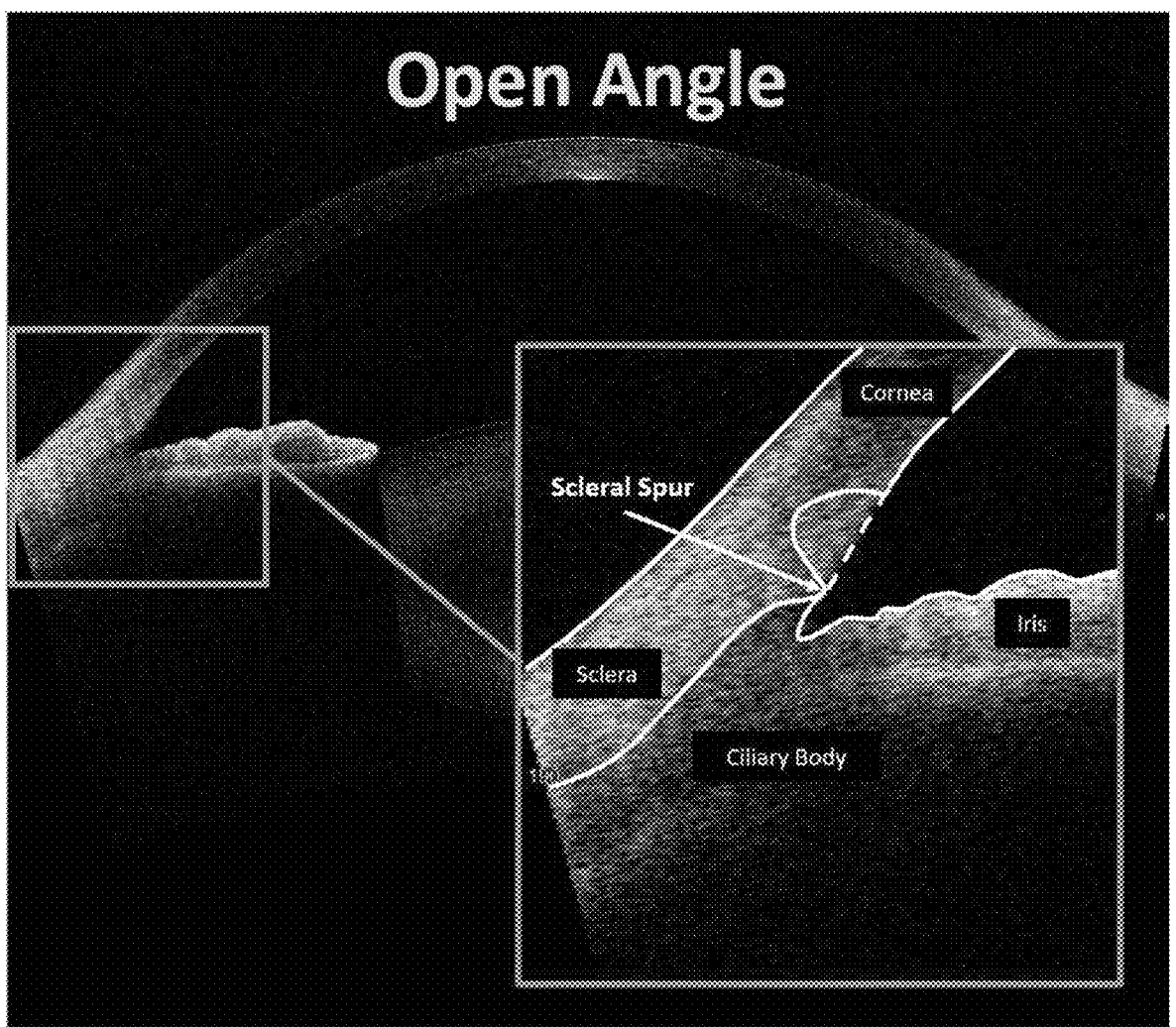
FIGS. 3A-3C depict examples of the scleral spur (SS) positions identified from the cross-sectional image at one of the scanned angle-locations in accordance with an embodiment of the subject invention with (3A) open angle structure, (3B) narrow angle structure, and (3C) closed angle structure, respectively. The SS usually lies at the posterior edge of the internal scleral sulcus, which can be identified as the intersection of the inner layer of the cornea and the anterior boundary between the sclera and the ciliary body in the AS-OCT cross-sectional scan.
Figure 3B:
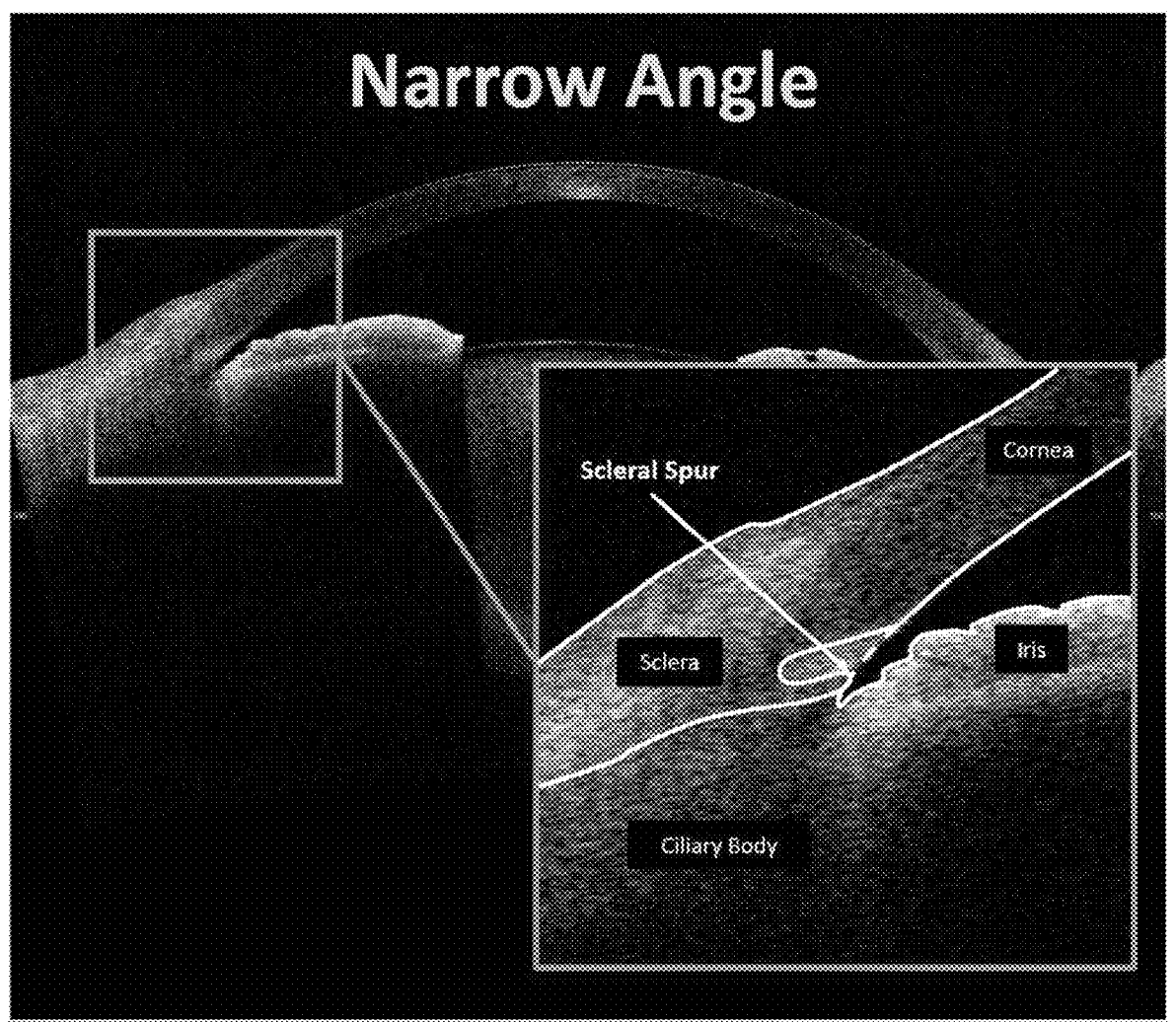
Figure 3C:
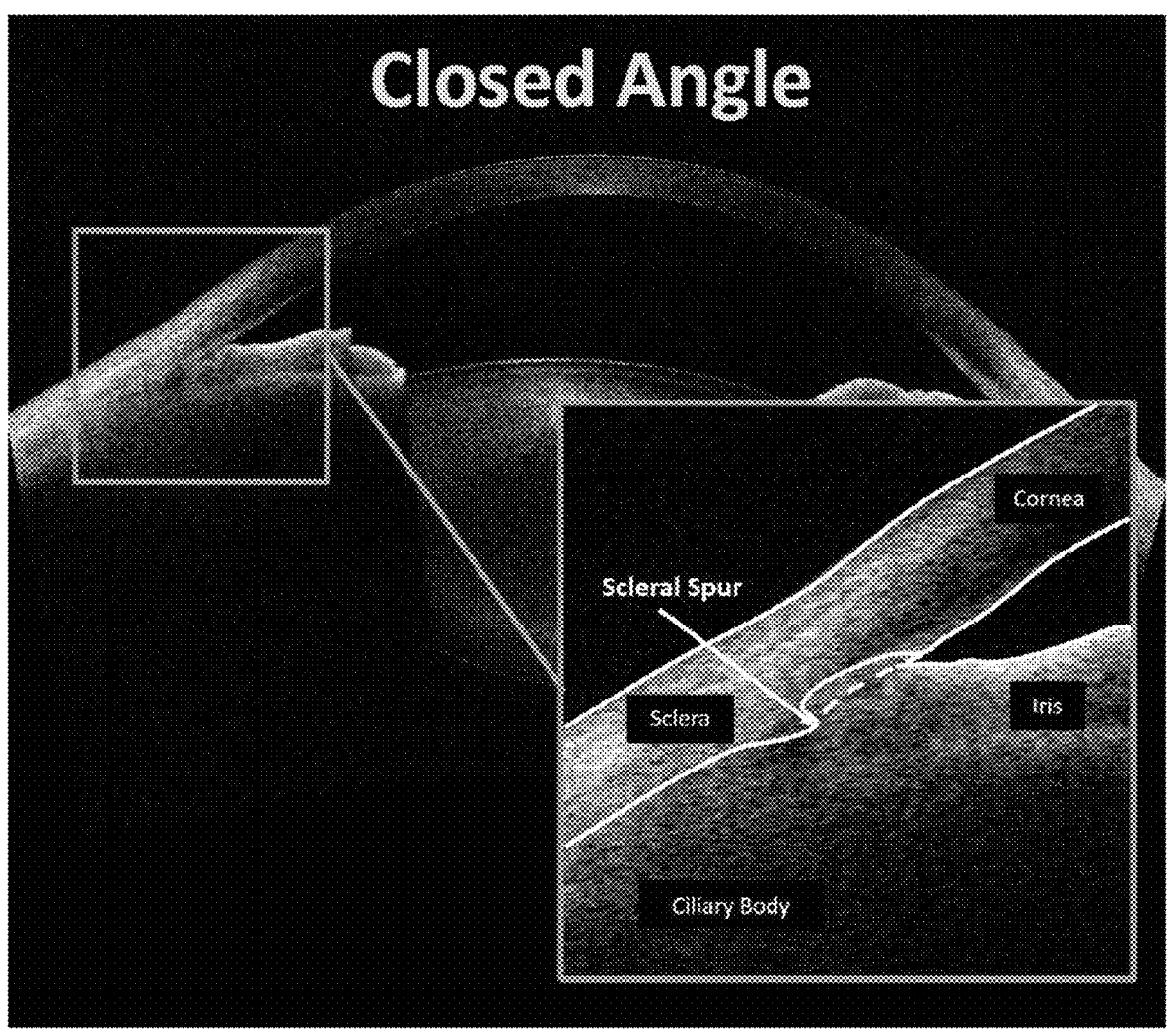
Figure 4A:
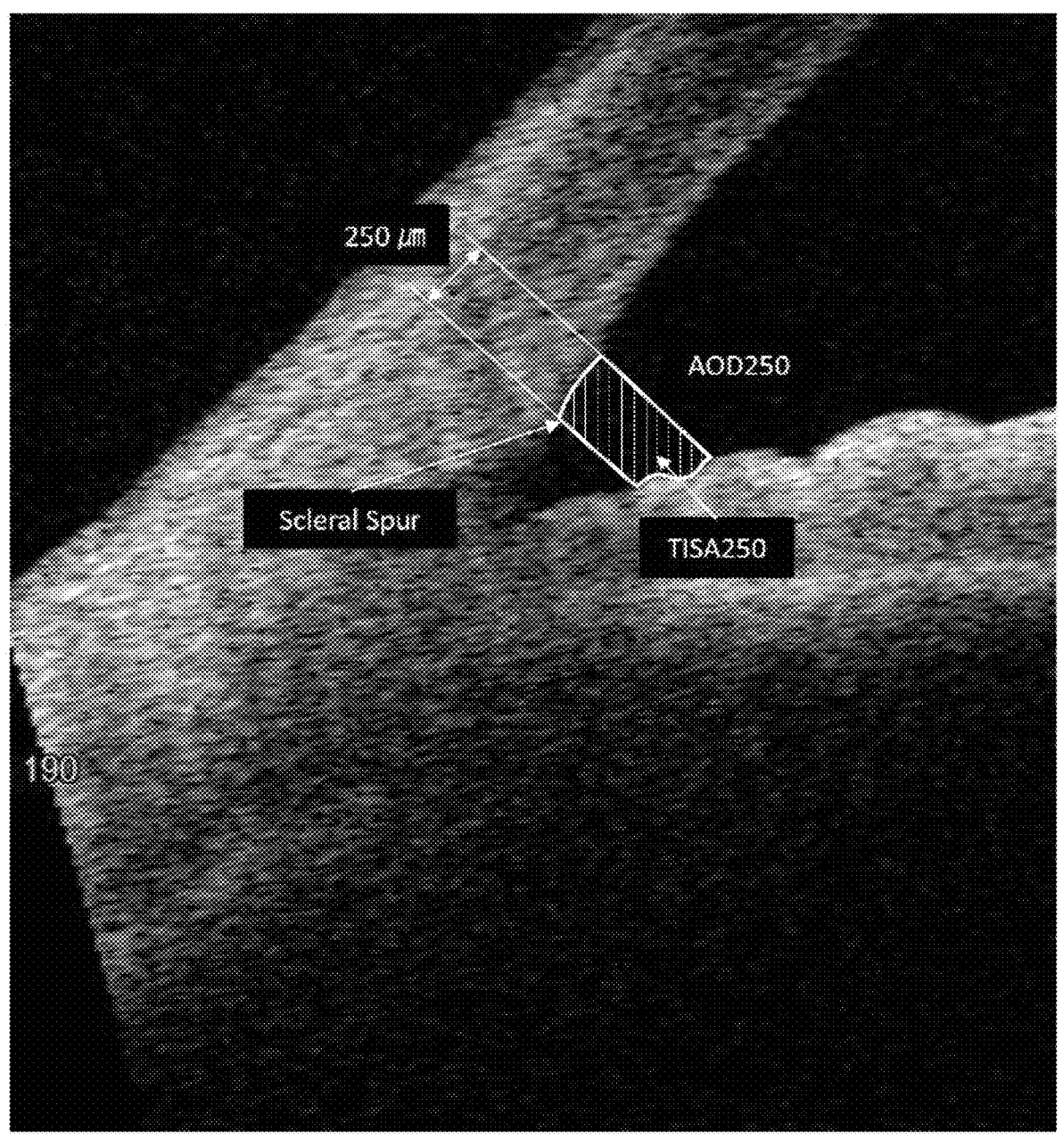
FIGS. 4A-4B illustrate measurements of anterior chamber angle (ACA) parameters (e.g. angle opening distance (AOD) or trabecular iris space area (TISA)) from the cross-sectional image at each of angle-locations based on the identified SS position in accordance with an embodiment of the subject invention.
Figure 4B:
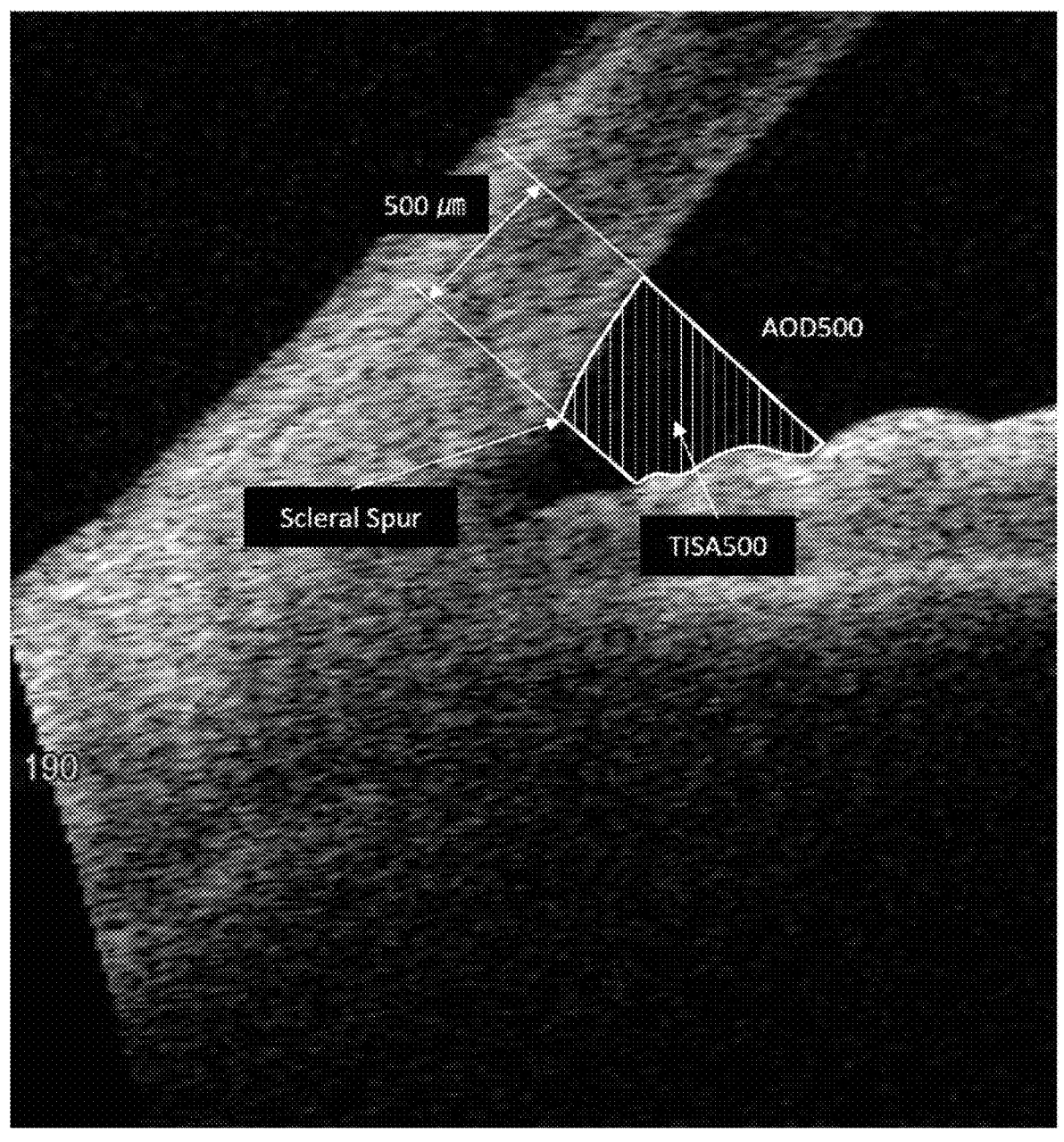

For example, embodiments of the subject invention can include receiving a plurality of cross-sectional scan images of the anterior segment of the patient's eye, wherein the plurality of images is acquired in preferably, but not necessarily, evenly spaced circumferential separations with reference to the central axis of pupil in one complete scan at a time, forming 360° imaging of the anterior segment as illustrated in an example embodiment shown in FIG. 2. The position of the SS is then identified from the cross-sectional image at each of the scanned angle-locations as shown in FIGS. 3A-3C. A set of ACA parameters can be measured from the cross-sectional image at each of angle-locations based on the identified SS position, and a respective value for each of the ACA parameters of the respective angle-location can be determined (e.g., measurements of AOD or TISA) as depicted in FIGS. 4A-4B. For each of the scanned angle-locations, it is then determined whether the respective ACA values that correspond to the respective angle-location exhibit abnormality in the patient's eye, and the respective ACA is classified as (i) closed angle if the ACA value is equal to zero, or (ii) narrow angle if the ACA value is below a respective threshold ACA value for the respective angle-location, or (iii) open angle if the ACA value is equal to or above the respective threshold ACA value for the respective angle-location. The extents of narrow angles and closed angles among all angle-locations across 360° are computed. Based on the extents of narrow angles, closed angles, or a combination of both, a regression model is applied to compute the risk of PAC/PACG development. Once the risk of PAC/PACG development has been identified, a disease prognosis and a treatment plan can be provided.

In some embodiments, the cross-sectional scan images of the anterior segment of the eye are obtained by an anterior segment optical coherence tomography (AS-OCT) device. As illustrated in an exemplary and non-limiting embodiment shown in FIG. 2, each eye can have, for example, 36 scanned angle-locations, with each angle-location spanning approximately 10°.

Figure 5:
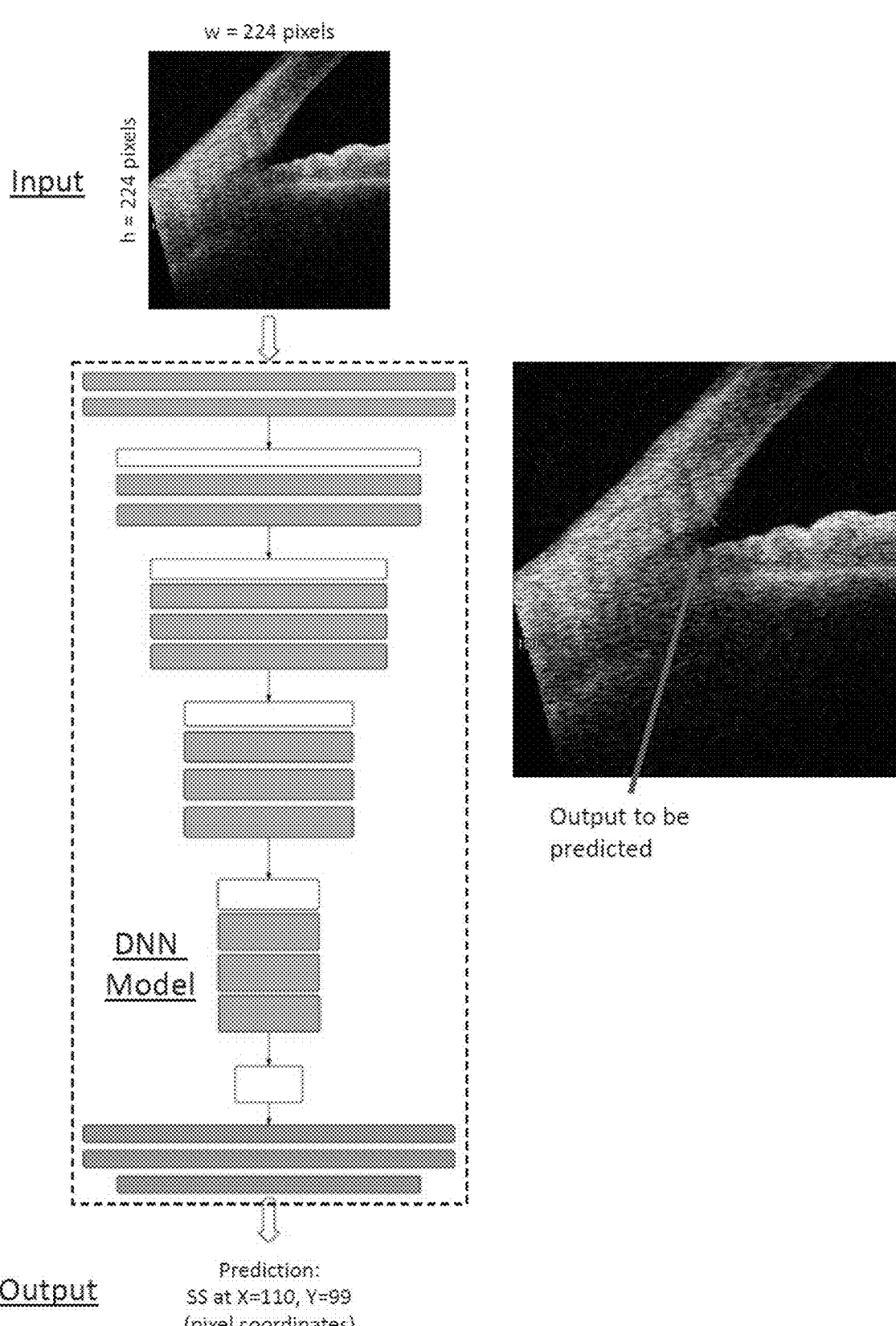
FIG. 5 illustrates a deep neural network model which can automatically detect the SS position from a cross-sectional OCT scan image at an angle-location of an eye and inform the pixel coordinates of the SS position on the image in accordance with an embodiment of the subject invention.
Figure 6A:
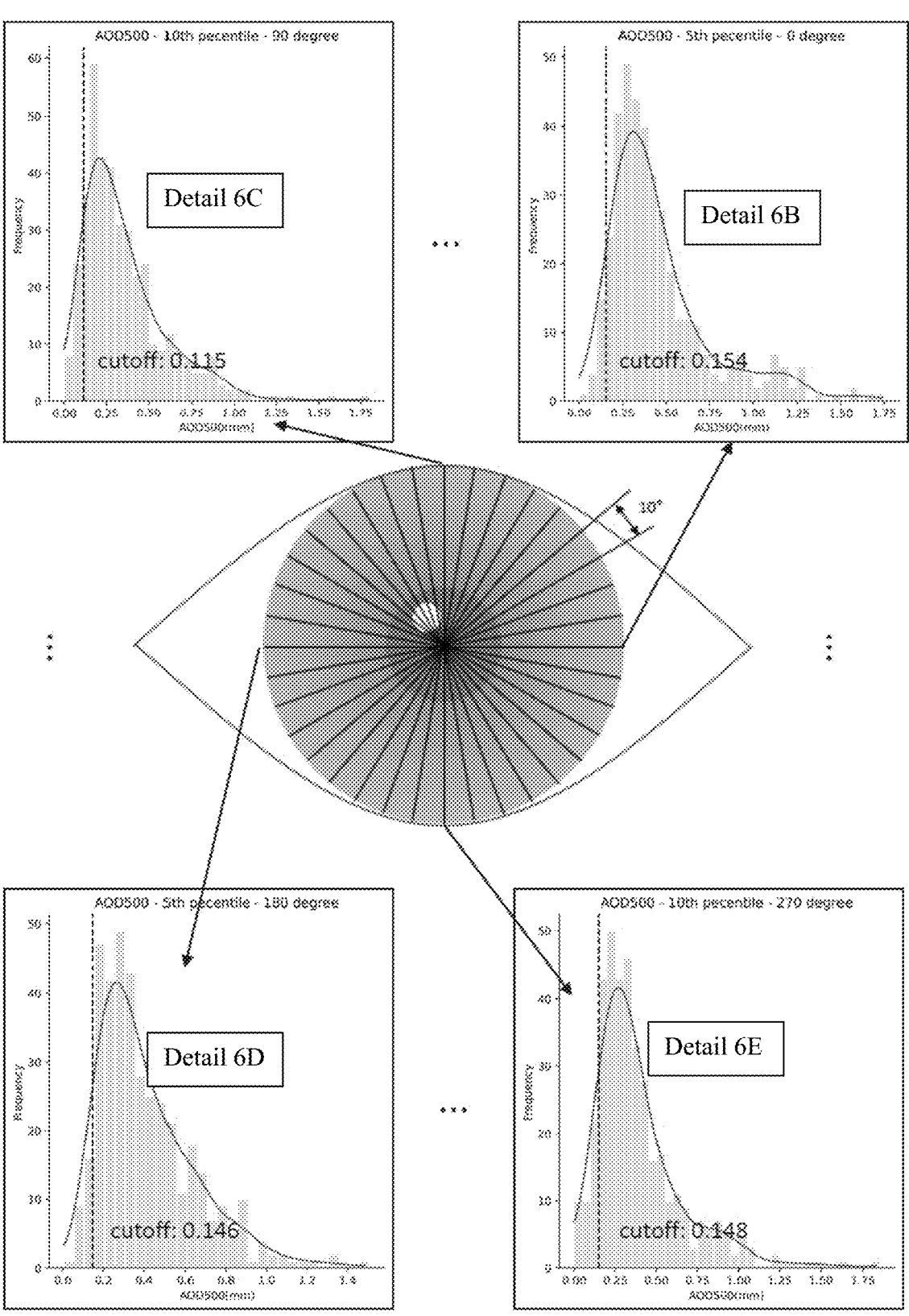
FIGS. 6A-6E depict how an example narrow angle threshold value is determined from the k-th percentile (e.g. $5^{th}$ percentile or $10^{th}$ percentile) of a normative distribution of the ACA parameter measured from healthy individuals of a specific age group in accordance with an embodiment of the subject invention.
Figure 6B:
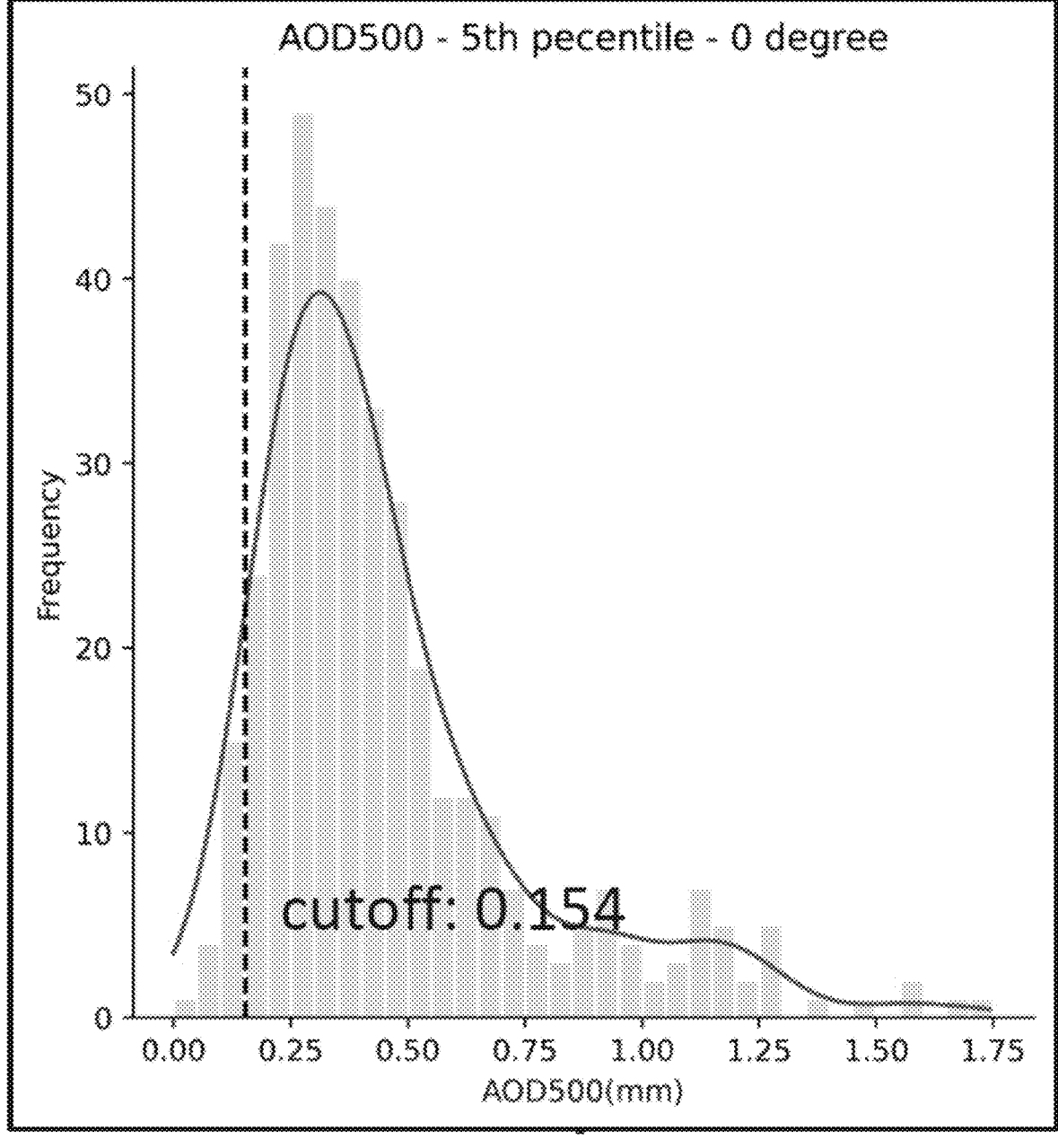
Figure 6C:
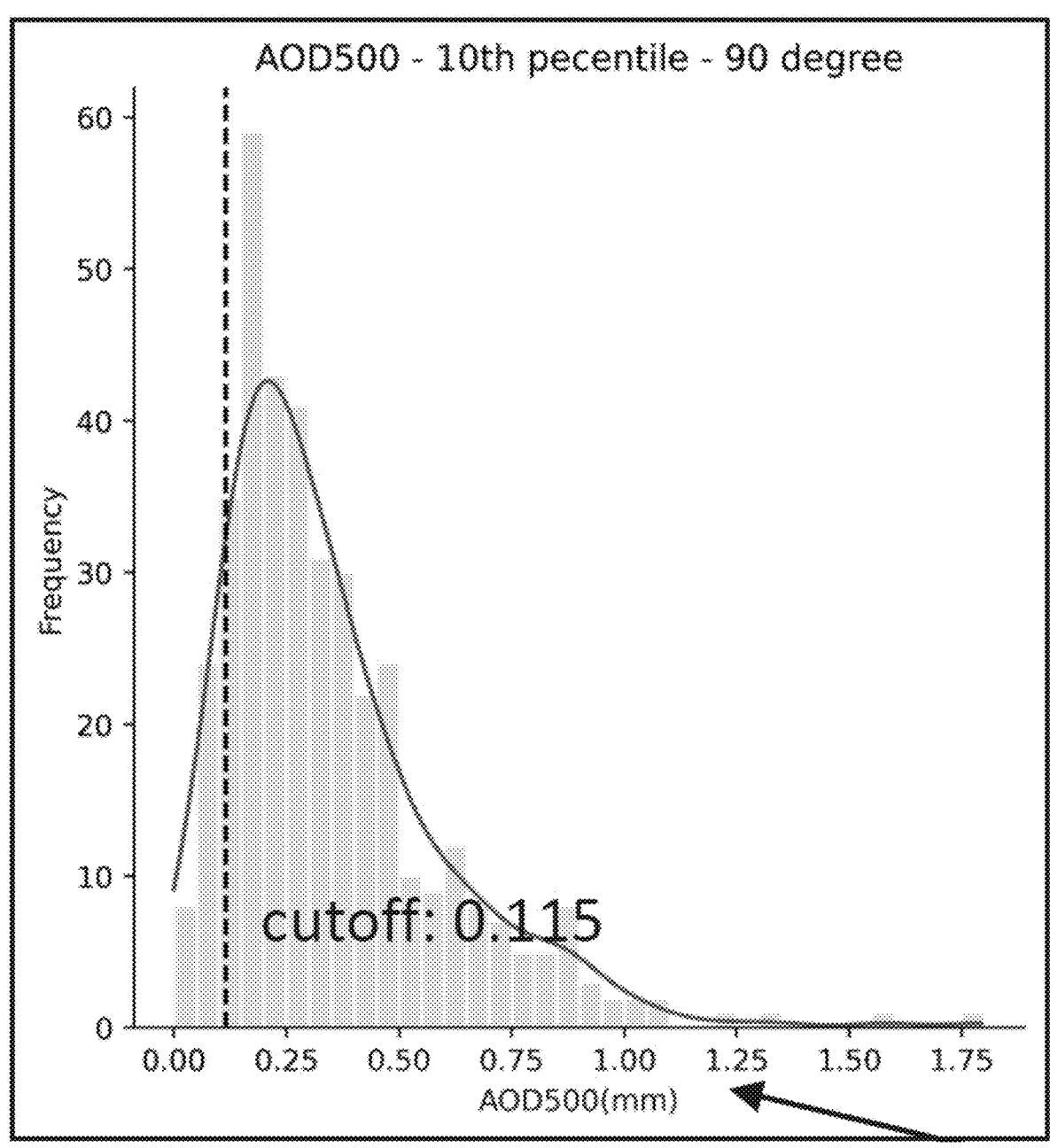
Figure 6D:
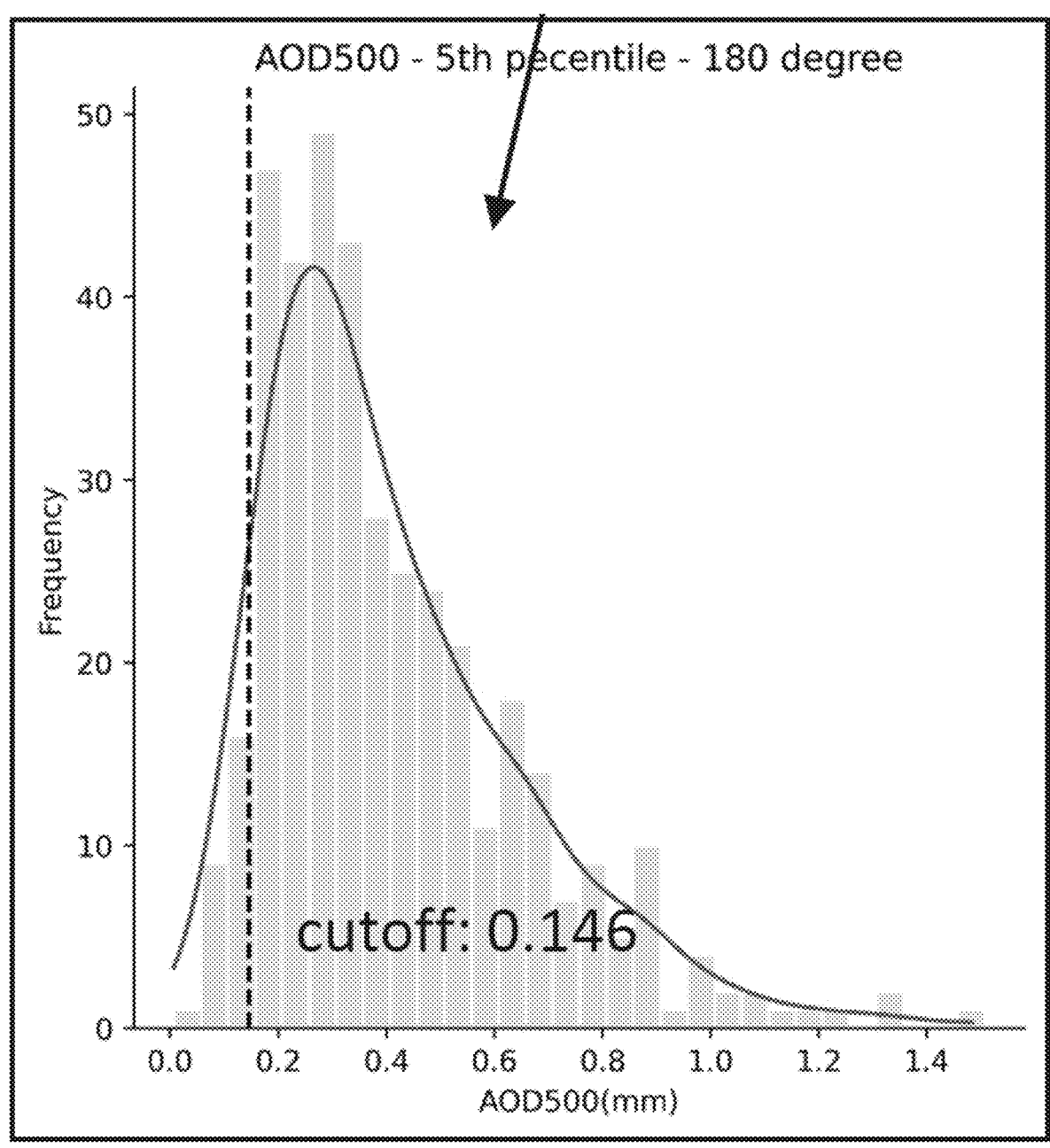
Figure 6E:
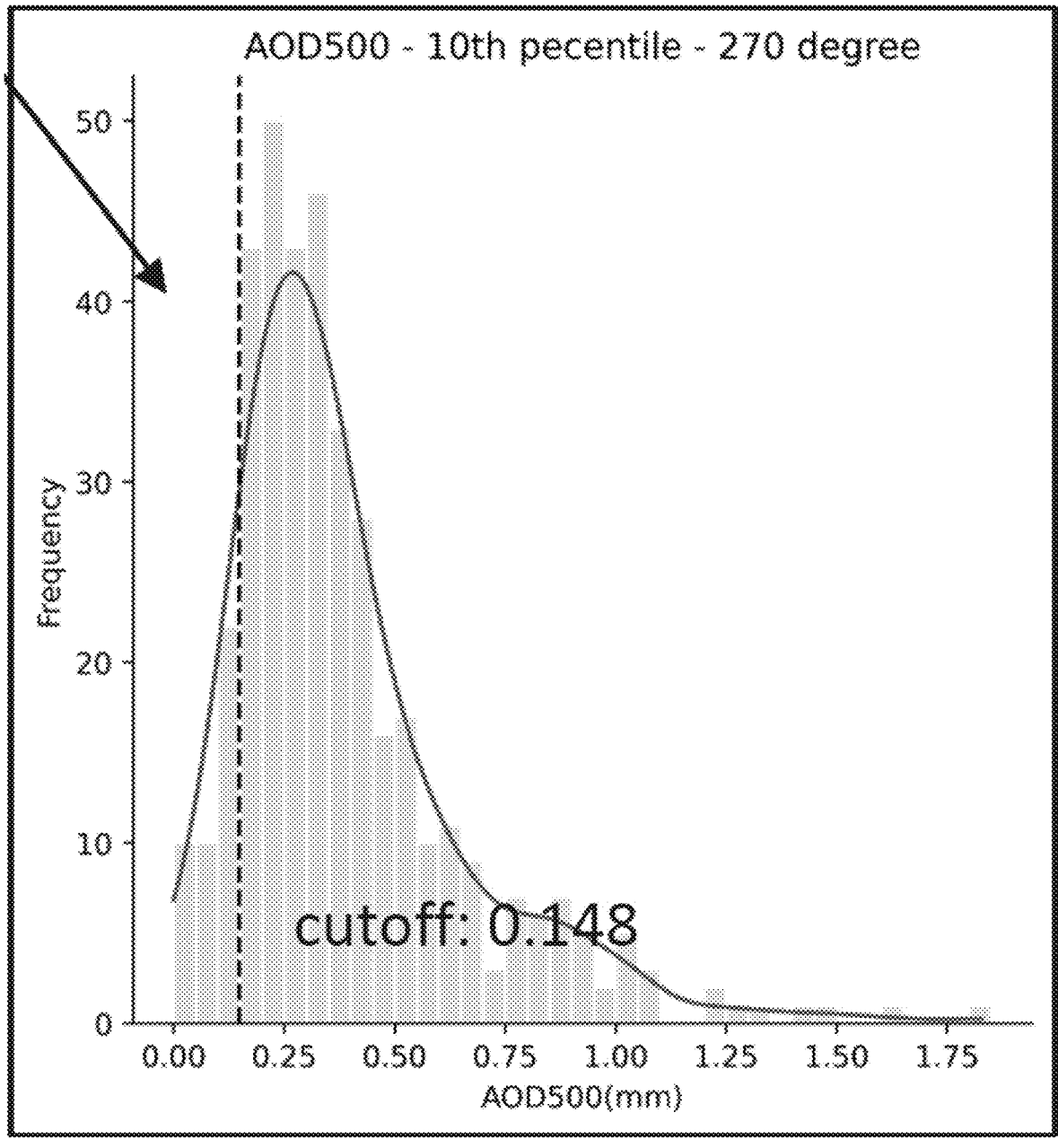

In some embodiments, the SS position can be detected manually by a human grader, or automatically using a deep neural network model trained with deep learning. As illustrated in FIG. 5, one exemplary and non-limiting example of the deep neural network model comprises an input module which receives the respective cross-sectional scan image of the respective angle-location, an output module which informs the pixel coordinates of the detected SS position on the respective cross-sectional scan image, and a set of intermediate layers consisting at least one convolutional layer, followed by at least one pooling layer, and further followed by at least one fully connected layer. An example model architecture that can be implemented is ResNet-50.

In further embodiments, the weights of intermediate layers are trained by a deep learning approach using a plurality of paired input-output examples, each paired example comprising a cross-sectional OCT scan image of the anterior segment as input, and a set of coordinates for ground-truth annotation of the SS position on the corresponding cross-sectional scan image as output. Throughout the training process, the best-performing set of weights can be determined by evaluating the Euclidean Distance (ED), which is the distance between the ground truth coordinates and the predicted coordinates, to assess the performance of the DNN models. The formula for ED calculation is:

$$ED = \frac{1}{n}\sum_{i=1}^{n}\left(\sqrt{(x_i - \tilde{x}_i)^2 + (y_i - \tilde{y}_i)^2}\right)$$

where $x_i$ and $y_i$ are the x-coordinate and y-coordinate of ground truth; $\tilde{x}_i$ and $\tilde{y}_i$ are the x-coordinate and y-coordinate of the estimated coordinate; n is the total number of SSs or corner points in the evaluation dataset.

In some embodiments, the ground-truth SS position for training the deep neural network model is labelled by one or more human graders. In some embodiments, the cross-sectional scan images of the training dataset include both images showing open angle structure and images showing closed angle structure. The images can be downsized or cropped to a target pixel resolution to adapt to the memory constraint of the system used to train the model.

In some embodiments, the plurality of measured ACA parameters for each scanned angle-location can include, but not limited to, one or more of the following:

(a) AOD at 250 μm from the SS (AOD250);
(b) AOD at 500 μm from the SS (AOD500);
(c) TISA at 250 μm from the SS (TISA250);
(d) TISA at 500 μm from the SS (TISA500).

For example, as shown in FIGS. 4A-4B, the AOD500 was measured as the perpendicular distance from the posterior corneoscleral junction at 500 μm anterior to the SS to the anterior iris surface. TISA500 represented the area bounded anteriorly by the AOD500, posteriorly by a line drawn from the SS perpendicular to the plane of the inner scleral wall to the opposing iris, superiorly by the inner corneoscleral wall, and inferiorly by the anterior iris surface.

In some embodiments, iris trabecular contact (ITC, or closed angle) of an angle-location was defined by AOD500=0 μmm and/or TISA500=0 μmm$^2$. A visible contact between the peripheral iris and the corneoscleral wall for at least 500 μm from the SS was required to define ITC because the trabecular meshwork length, measured from the SS to the Schwalbe's line, has been estimated to be about 575 μm in eyes with gonioscopic angle closure (Choi W, et al. Comparison of the trabecular meshwork length between open and closed angle with evaluation of the scleral spur location. Sci Rep. 2019; 9:6857). The iris can be out of apposition with the posterior trabecular meshwork if the contact between the iris and the angle wall is less than 500 μm. The extent of ITC (or closed angle) of an eye was estimated from the number of angle-locations with AOD500=0 μmm and/or TISA500=0 μmm$^2$.

In some embodiments, the threshold ACA value of an angle-location is determined from a specific cut-off percentile of the age-related distribution of that particular angle-location. The age-related distribution can be determined from a cross-sectional dataset collected from a normal healthy cohort. For example, measurements of ACA values are collected from a cohort of 300 healthy individuals, which is composed of 6 age groups: 18-30 years, 31-40 years, 41-50 years, 51-60 years, 61-70 years, and >70 years. There are 50 subjects recruited for each age group, forming an age group-specific normative distribution for each ACA parameter at each angle-location.

In further embodiments, an age group-specific k-th percentile of a selected ACA parameter is derived from the age group-specific normative distribution for each angle-location. This k-th percentile is used to define the threshold value of the selected ACA parameter at the angle-location where the ACA is determined as narrow angle when the measured value of the selected ACA parameter is below this threshold. For example, in certain exemplary and non-limiting embodiments, the k-th percentile can be (but is not limited to) the 5$^{th}$ or the 10$^{th}$ percentile of the distribution as shown in FIGS. 6A-6E. In some embodiments, the k-th percentile used to determine the threshold ACA value at one angle-location is not necessarily the same as the percentile used to determine the threshold ACA value at other angle-locations.

Figure 9:
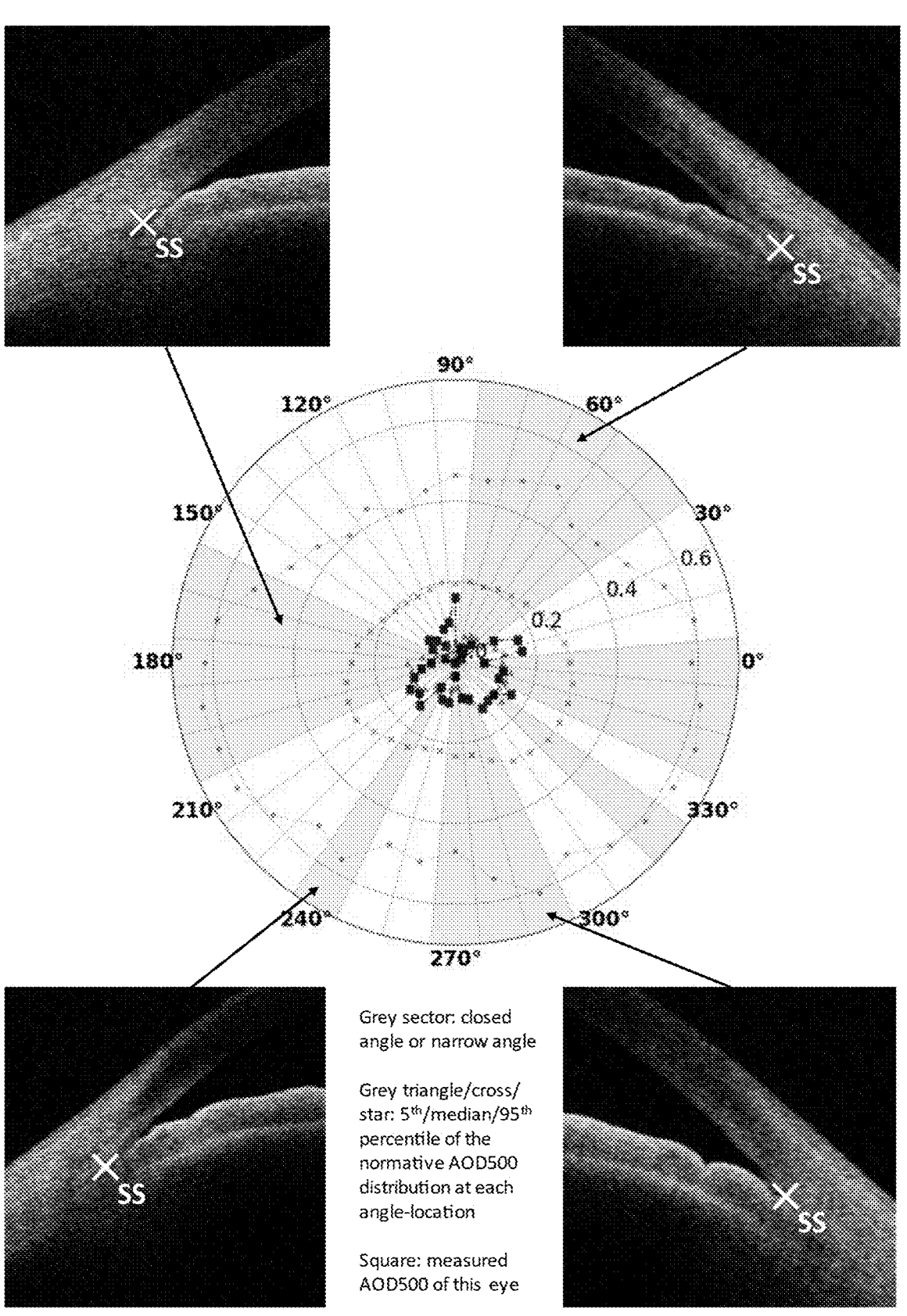
FIG. 9 depicts an example polar plot of AOD500 μmeasurements at different angle-locations from an eye detected with gonioscopic angle closure showing extensive ACA abnormalities, alongside with the $95^{th}$ percentile, median, and $5^{th}$ percentile of the normative distribution for the age-group of the eye at each measured angle-locations in accordance with an embodiment of the subject invention.
Figure 10:
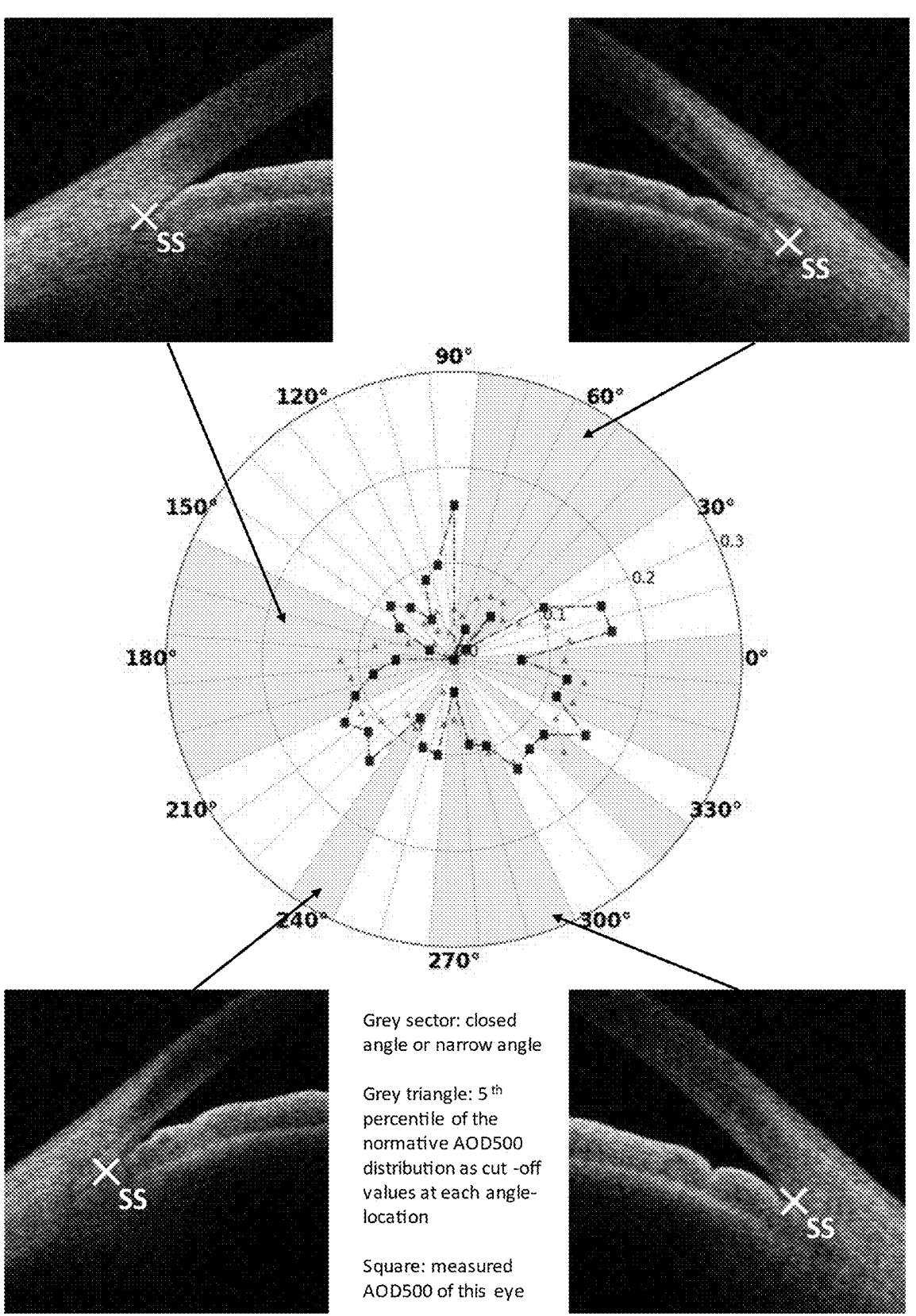
FIG. 10 illustrates a rescaled version of the polar plot in FIG. 9 with a magnified scale of the radial axis, showing only the measured AOD500 values and the age group-specific $5^{th}$ percentiles of the measured angle-locations in accordance with an embodiment of the subject invention.
Figure 11:
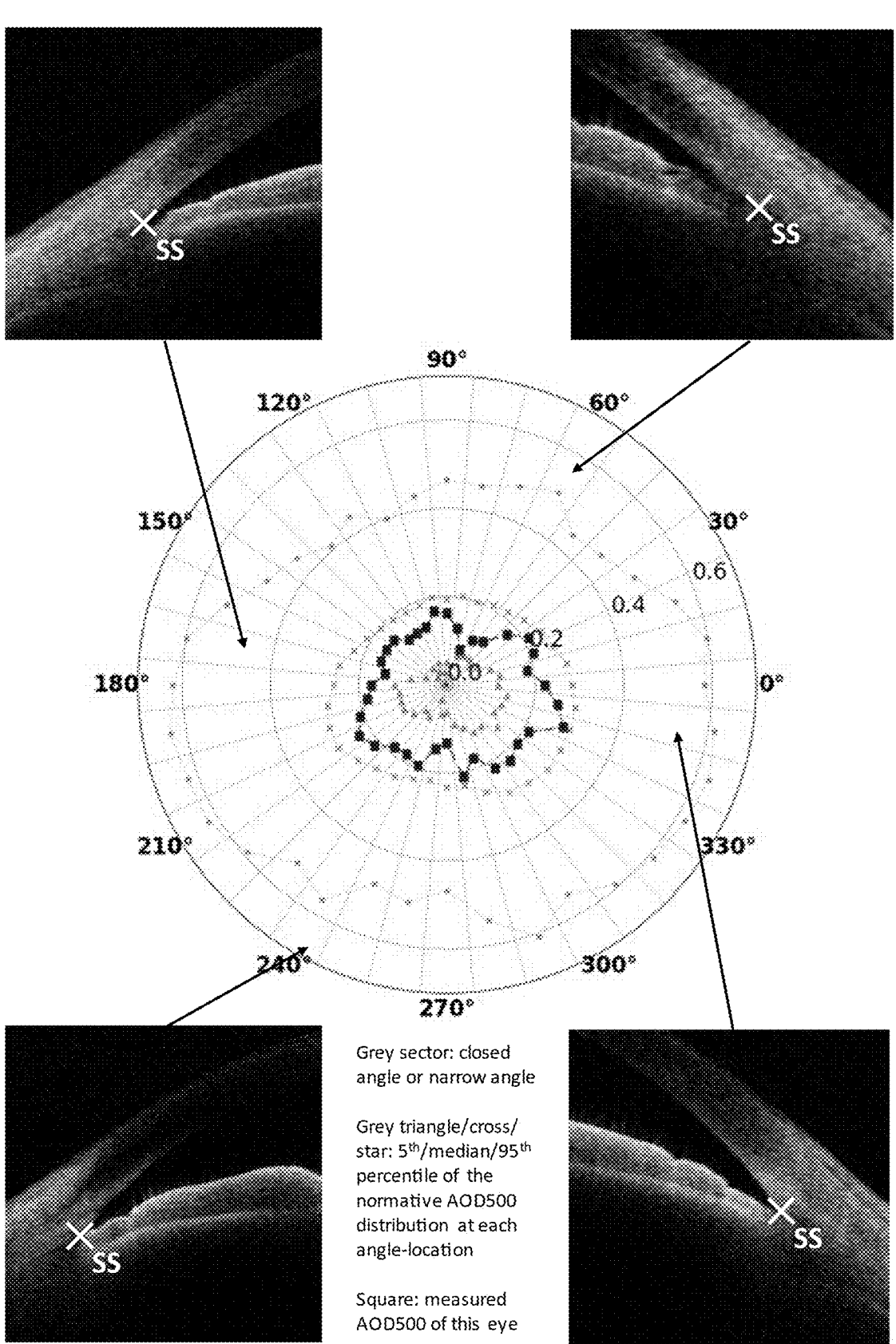
FIG. 11 depicts an example polar plot of AOD500 measurements at different angle-locations from a healthy eye without any ACA abnormality in accordance with an embodiment of the subject invention.

As an illustrative example, the AOD500 measurements at 36 angle-locations from an eye detected with gonioscopic angle closure are plotted as a polar plot in FIG. 9, showing extensive ACA abnormalities. The radial axis represents AOD500 in the unit of mm and each sector represents one of the 36 measured angle-locations. Each dark solid square symbol denotes an AOD500 value measured at the respective angle-location from the example eye. On the other hand, the normative AOD500 values from the age-group of the eye are plotted in the same polar plot with each grey star symbol denoting the 95$^{th}$ percentile of the age group-specific normative distribution for an angle-location, each grey cross symbol denoting the median, and each grey triangle denoting the 5$^{th}$ percentile. FIG. 10 illustrates a magnified version of the polar plot in FIG. 9, showing only the measured AOD500 values and the age group-specific 5$^{th}$ percentiles of the measured angle-locations. In this example, the age group-specific 5$^{th}$ percentile is used as the cut-off percentile to determine if the ACA of an angle-location is a narrow angle for all angle-locations. When the measured AOD500 value is below the age group-specific 5$^{th}$ percentile or equal to zero at an angle-location, the respective sector of the polar plot is highlighted in grey color. The extent of ACA abnormalities is calculated based on the total number of narrow/closed angles detected from the eye. On the contrary, an example demonstrating an eye without any ACA abnormality is illustrated in FIG. 11. None of the angle-locations has the measured AOD500 value below the respective age group-specific 5$^{th}$ percentile in this eye.

Figure 7:
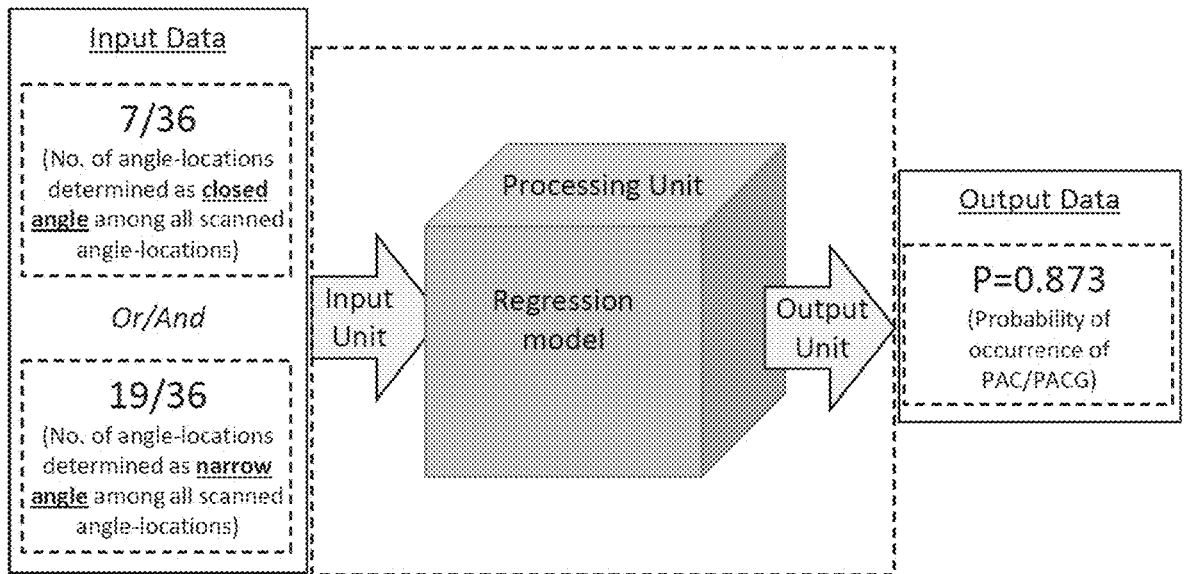
FIG. 7 illustrates a regression model used to predict the risk of disease development from the extent of abnormalities based on the ACA in accordance with an embodiment of the subject invention.

In some embodiments, the regression model is a logistic regression model or a machine learning model predicting the risk of disease development from the extent of abnormalities based on the ACA, as demonstrated in FIG. 7. The extent of abnormalities can be determined based on the number of narrow angles among all angle-locations, the number of closed angles among all angle-locations, or a combination of both. In further embodiments, the risk of disease development is estimated using the odds ratio computed from the logistic regression model based on the determined extent of ACA abnormalities in the eye.

When the regression model is a logistic regression model and the extent of abnormalities is based on a number of narrow angles only or a number of closed angles only, the logistic regression model can be expressed as follows:

$$\text{logit}[\pi(X)] = \beta_0 + \beta_1 X_1$$

where the logit function is the quantile function associated with the standard logistic distribution, X represents the total number of angles measured (closed, narrow, or open), $\beta_0$ and $\beta_1$ are predetermined constants, and $X_1$ represents either the number of narrow angles or number of closed angles accordingly. In certain embodiments the logit function refers to the logistic quantile function, which is used in logistic regression model to determine the cutoff number of narrow/closed angle locations for detecting angle-closure.

Alternatively, when the regression model is a logistic regression model and the extent of abnormalities is based on a combination of both the number of narrow angles and the number of closed angles, the logistic regression model can be expressed as follows:

$$\text{logit}[\pi(X)] = \beta_0 + \beta_1 X_1 + \beta_2 X_2$$

where $X_1$ represents the number of narrow angles, $X_2$ represents the number of closed angles, while $\beta_1$ and $\beta_2$ represents different weights for the number of narrow angles ($X_1$) and the number of closed angles ($X_2$) in the model.

Other embodiments can include dividing the scanned angle-locations of the eye into a plurality of angle-location partitions, where each angle-location partition includes one or more adjacent angle-locations. For instance, the 360° radial space can be divided into one of the following, including but not limited to: 2 partitions of angle-locations with each partition covering 180°; 4 partitions of angle-locations with each partition covering 90°; 6 partitions of angle-locations with each partition covering 60°; or each partition can just include one angle-location. For each angle-location partition, a partition-specific extent of abnormalities among all angle-locations in the partition can be calculated, wherein the extent of abnormalities is calculated from any of the following:

(a) the number of angle-locations determined as closed angle;

(b) the number of angle-locations determined as narrow angle; or (c) a combination of (a) and (b);

In further embodiments, the risk of PAC/PACG development for the eye is determined from a regression model based on the plurality of partition-specific extents of ACA abnormalities. The regression model can be a logistic regression model or a machine learning model predicting the risk of disease development from the plurality of partition-specific extents of ACA abnormalities, with different partitions contributing to different weights, which can be expressed as follows:

$$\text{logit}[\pi(X)] = \beta_0 + \beta_1 X_1 + \beta_2 X_2 + \ldots + \beta_p X_p$$

where $X_1$ represents the number of narrow/closed angles in the $1^{st}$ partition, $X_2$ represents the number of narrow and/or closed angles in the $2^{nd}$ partition, and $X_p$ represents the number of narrow and/or closed angles in the p-th partition when the angle-locations are divided into p partitions. The risk of disease development can be estimated using the odds ratio computed from the logistic regression model based on the plurality of extents of ACA abnormalities in the eye.

Alternatively, a regression model can be computed for each angle-location partition set from the respective extent of abnormalities in the angle-location partition. A partition can then be classified as normal or abnormal based on the extents of narrow and/or closed angles among that particular partition. Another regression model can be computed based on the number of abnormal partitions.

In some embodiments, when the regression model is a machine learning model, the model is a deep neural network (DNN) model predicting the risk of PAC/PACG development from a plurality of classifications of open/narrow/closed angle for the ACA at each scanned angle-location. In some embodiments, the regression model is a deep neural network model predicting the risk of disease development from a plurality of one or more selected ACA parameter values at each scanned angle-location.

Figure 8:
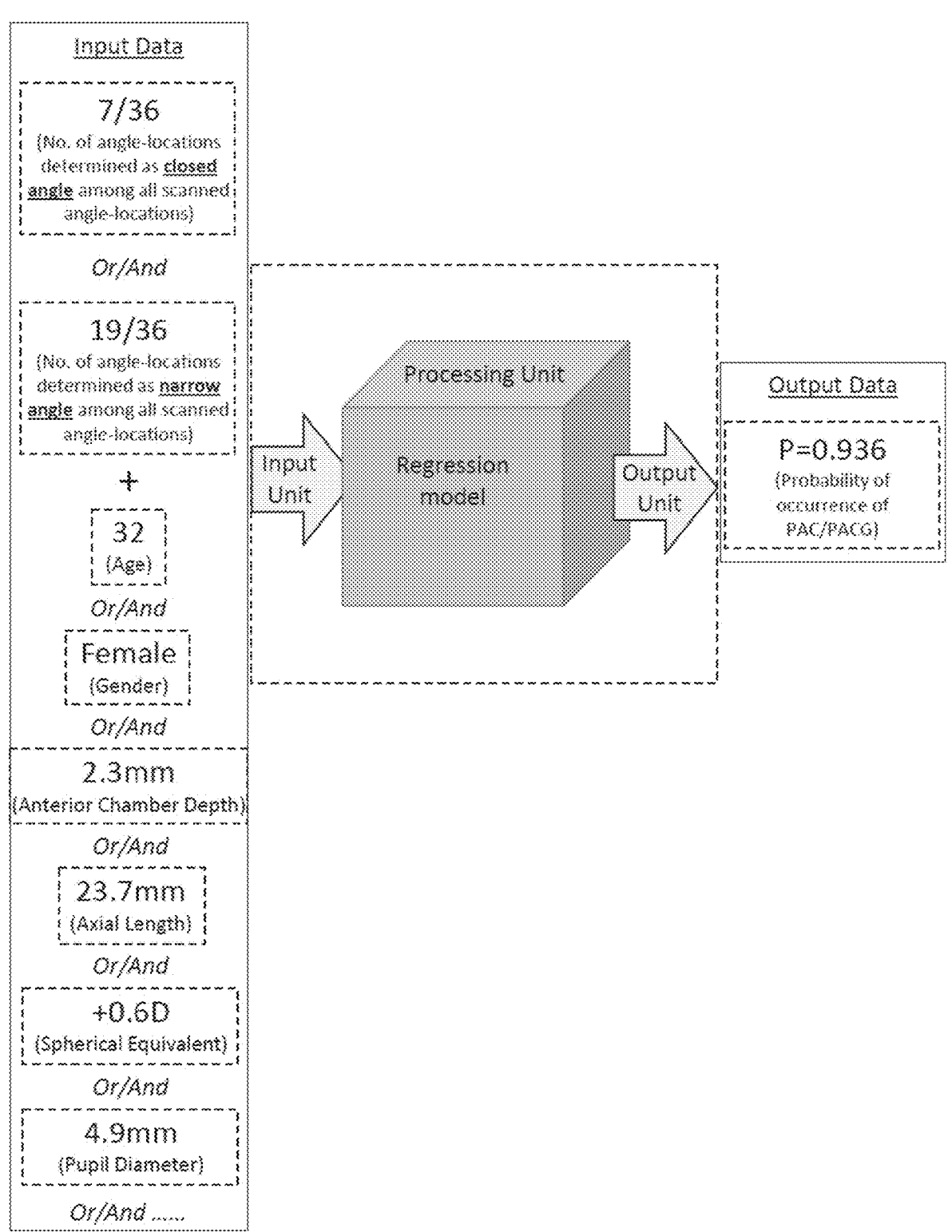
FIG. 8 illustrates a regression model used to predict the risk of disease development for the eye further based on additional example information of the patient and the eye in accordance with an embodiment of the subject invention.

In some embodiments, as illustrated in FIG. 8, the regression model determines the risk of disease development for the eye further based on additional information of the patient and the eye including, but not limited to, any of the following:

(a) age;

(b) gender;

(c) anterior chamber depth;

(d) spherical equivalent;

(e) axial length;

(f) pupil diameter; or (g) a combination of any two or more of (a) to (f).

Aspects of the invention may be described in the general context of computer-executable instructions, such as program modules, being executed by a computer. Generally, program modules include routines, programs, objects, components, data structures, etc., that perform particular tasks or implement particular abstract data types. Moreover, those skilled in the art will appreciate that the invention may be practiced with a variety of computer-system configurations, including multiprocessor systems, microprocessor-based or programmable-consumer electronics, minicomputers, mainframe computers, and the like. Any number of computer systems and computer networks are acceptable for use with the subject invention.

Specific hardware devices, programming languages, components, processes, protocols, and numerous details including operating environments and the like are set forth to provide a thorough understanding of the subject invention. In other instances, structures, devices, and processes are shown in block-diagram form, rather than in detail, to avoid obscuring the subject invention. But an ordinary-skilled artisan would understand that the subject invention may be practiced without these specific details. Computer systems, servers, workstations, and other machines may be connected to one another across a communication medium including, for example, a network or networks.

As one skilled in the art will appreciate, embodiments of the subject invention may be embodied as, among other things: a method, system, or computer-program product. Accordingly, the embodiments may take the form of a hardware embodiment, a software embodiment, or an embodiment combining software and hardware. In an embodiment, the subject invention takes the form of a computer-program product that includes computer-useable instructions embodied on one or more computer-readable media.

Computer-readable media include both volatile and non-volatile media, transitory and non-transitory, transient and non-transient media, removable and nonremovable media, and contemplate media readable by a database, a switch, and various other network devices. By way of example, and not limitation, computer-readable media comprise media implemented in any method or technology for storing information. Examples of stored information include computer-useable instructions, data structures, program modules, and other data representations. Media examples include, but are not limited to, information-delivery media, RAM, ROM, EEPROM, flash memory or other memory technology, CD-ROM, digital versatile disks (DVD), holographic media or other optical disk storage, magnetic cassettes, magnetic tape, magnetic disk storage, and other magnetic storage devices. These technologies can store data momentarily, temporarily, or permanently.

The invention may be practiced in distributed-computing environments where tasks are performed by remote-processing devices that are linked through a communications network. In a distributed-computing environment, program modules may be located in both local and remote computer-storage media including memory storage devices. The computer-useable instructions form an interface to allow a computer to react according to a source of input. The instructions cooperate with other code segments to initiate a variety of tasks in response to data received in conjunction with the source of the received data.

The subject invention may be practiced in a network environment such as a communications network. Such networks are widely used to connect various types of network elements, such as routers, servers, gateways, and so forth.

Further, the invention may be practiced in a multi-network environment having various, connected public and/or private networks.

Communication between network elements may be wireless or wireline (wired). As will be appreciated by those skilled in the art, communication networks may take several different forms and may use several different communication protocols. And the subject invention is not limited by the forms and communication protocols described herein.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application.

Embodiments of the subject invention address the technical problem of limitations and complexities inherent in related art approaches to primary angle closure (PAC) or primary angle closure glaucoma (PACG) detection, diagnosis, and treatment causing available systems and methods to be expensive, to require excessive human processing, and to be unreliable. This problem, and the inherent limitations and complexities, is addressed by providing novel digital image processing, abnormality classification, and analysis based on anterior chamber angle (ACA) parameters, in which a regression model applying a combination of advanced techniques is utilized to identify, diagnose, determine risk of, treat, provide methods of treating, or guide the treatment of PAC or PACG.

The transitional term "comprising," "comprises," or "comprise" is inclusive or open-ended and does not exclude additional, unrecited elements or method steps. By contrast, the transitional phrase "consisting of" excludes any element, step, or ingredient not specified in the claim. The phrases "consisting" or "consists essentially of" indicate that the claim encompasses embodiments containing the specified materials or steps and those that do not materially affect the basic and novel characteristic(s) of the claim. Use of the term "comprising" contemplates other embodiments that "consist" or "consisting essentially of" the recited component(s).

When ranges are used herein, such as for dose ranges, combinations and subcombinations of ranges (e.g., sub-ranges within the disclosed range), specific embodiments therein are intended to be explicitly included. When the term "about" is used herein, in conjunction with a numerical value, it is understood that the value can be in a range of 95% of the value to 105% of the value, i.e., the value can be +/−5% of the stated value. For example, "about 1 kg" means from 0.95 kg to 1.05 kg.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processor reads and executes the code and/or data stored on a computer-readable medium, the computer system and/or processor performs the methods and processes embodied as data structures and code stored within the computer-readable storage medium.

It should be appreciated by those skilled in the art that computer-readable media include removable and non-re-movable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

A greater understanding of the embodiments of the subject invention and of their many advantages may be had from the following examples, given by way of illustration. The following examples are illustrative of some of the methods, applications, embodiments, and variants of the present invention. They are, of course, not to be considered as limiting the invention. Numerous changes and modifications can be made with respect to embodiments of the invention.

Embodiment 1. A method for analyzing an anterior segment of an eye to estimate the risk of development of primary angle closure and primary angle closure glaucoma in a patient, the method comprising:

receiving a plurality of cross-sectional scan images of the anterior segment of the eye, wherein each respective image represents a different circumferential angle-location with reference to a central axis of a pupil of the eye, with spaced circumferential separation between respective images across the 360° radial space;

locating a plurality of scleral spur (SS) positions, wherein each respective SS position is located on a respective cross-sectional scan image of a respective angle-location;

measuring a plurality of anterior chamber angle (ACA) parameters for each respective angle-location based on the SS position of the respective angle-location;

classifying each respective angle-location as either normal or abnormal based on one respective ACA parameter of the plurality of measured ACA parameters;

calculating an extent of abnormalities with reference to the total number of abnormal angle-locations; and determining a risk of disease development for the eye from a regression model based on the extent of abnormalities.

Embodiment 2. The method of Embodiment 1, wherein the plurality of cross-sectional scan images of the anterior segment is captured using an optical coherence tomography (OCT) instrument.

Embodiment 3. The method of Embodiment 1, wherein the SS position on the cross-sectional scan image of each respective angle-location is located manually by a human grader or automatically by a machine learning model.

Embodiment 4. The method of Embodiment 3, wherein the machine learning model is a trained deep neural network comprising:

an input module which receives the respective cross-sectional scan image of the respective angle-location;

an output module which informs the pixel coordinates of the located SS position on the respective cross-sectional scan image; and a set of intermediate layers consisting at least one convolutional layer, followed by at least one pooling layer, and further followed by at least one fully connected layer.

Embodiment 5. The method of Embodiment 4, wherein the deep neural network is trained by a supervised learning approach using a plurality of paired input-output examples, each paired input-output example comprising a cross-sectional scan image of an anterior segment as input, and a set of coordinates for ground-truth location of the SS position on the corresponding cross-sectional scan image labelled by one or more human graders as output.

Embodiment 6. The method of Embodiment 1, wherein the plurality of measured ACA parameters for each angle-location comprises AOD250, AOD500, TISA250, and TISA500.

Embodiment 7. The method of Embodiment 1, wherein each respective abnormal angle-location is further classified as either closed angle or narrow angle based on one respective ACA parameter of the plurality of measured ACA parameters.

Embodiment 8. The method of Embodiment 7, wherein each respective abnormal angle-location is classified as closed angle when the value of the respective ACA parameter is equal to zero.

Embodiment 9. The method of Embodiment 7, wherein each respective abnormal angle-location is classified as narrow angle when the value of the respective ACA parameter is below a respective threshold value for the respective angle-location.

Embodiment 10. The method of Embodiment 9, wherein the respective threshold value for the respective angle-location is determined from a pre-determined cut-off percentile of a normative distribution of the respective ACA parameter measured at the respective angle-location.

Embodiment 11. The method of Embodiment 10, wherein the normative distribution is comprised of a cross-sectional dataset with measurements collected from a cohort of normal eyes from healthy individuals.

Embodiment 12. The method of Embodiment 10, wherein the normative distribution is specific to an age group corresponding to the patient.

Embodiment 13. The method of Embodiment 10, wherein a first pre-determined cut-off percentile of the normative distribution of the respective ACA parameter at a first respective angle-location is not constrained to be the same as a second pre-determined cut-off percentile of the normative distribution of the respective ACA parameter at a second respective angle-location.

Embodiment 14. The method of Embodiment 7, wherein the extent of abnormalities is calculated from any of:

(a) total number of angle-locations classified as closed angle;

(b) total number of angle-locations classified as narrow angle; or (c) a combination of (a) and (b).

Embodiment 15. The method of Embodiment 1, wherein the regression model comprises either a logistic regression model or a machine learning model and predicts the probability of disease occurrence for determining the risk of disease development.

Embodiment 16. The method of Embodiment 15, wherein the regression model is a logistic regression model and the probability of disease occurrence is predicted using an odds ratio computed from the regression model based on the extent of ACA abnormalities in the eye.

Embodiment 17. The method of Embodiment 7, further comprising:

dividing the scanned angle-locations of the eye into a plurality of evenly spaced angle-location partitions, wherein each angle-location partition includes one or more adjacent angle-locations;

calculating a partition-specific extent of ACA abnormalities among all angle-locations for each respective angle-location partition, wherein the partition-specific extent of abnormalities is calculated from any of:

(a) total number of angle-locations classified as closed angle;

(b) total number of angle-locations classified as narrow angle; or (c) a combination of (a) and (b); and determining the risk of disease development for the eye from a regression model based on the plurality of partition-specific extents of ACA abnormalities.

Embodiment 18. The method of Embodiment 17, wherein the regression model is either a logistic regression model or a machine learning model which predicts the probability of disease occurrence for determining the risk of disease development and wherein for each respective angle-location partition the respective partition-specific extent of abnormalities is multiplied by a respective weighting factor for the respective partition.

Embodiment 19. The method of Embodiment 18, wherein the regression model is a logistic regression model and the probability of disease occurrence is estimated using an odds ratio computed from the regression model based on the plurality of partition-specific extents of ACA abnormalities in the eye.

Embodiment 20. The method of Embodiment 17, wherein the regression model determines the risk of disease development for the eye further based on additional information of the patient or the eye comprising at least one of:

(a) age;

(b) gender;

(c) anterior chamber depth;

(d) spherical equivalent;

(e) axial length;

(f) pupil diameter; or (g) a combination of any two or more of (a) to (f).

We claim:

1. A method for analyzing an anterior segment of an eye to estimate the risk of development of a disease of the eye in a patient, the disease of the eye comprising at least one of primary angle closure and primary angle closure glaucoma, the method comprising:

receiving a plurality of cross-sectional scan images of the anterior segment of the eye, wherein each respective image represents a different circumferential angle-location with reference to a central axis of a pupil of the eye, with spaced circumferential separation between respective images across the 360° radial space;

locating a plurality of scleral spur (SS) positions, wherein each respective SS position is located on a respective cross-sectional scan image of a respective angle-location;

measuring a plurality of anterior chamber angle (ACA) parameters for each respective angle-location based on the SS position of the respective angle-location;

classifying each respective angle-location as either normal or abnormal based on one respective ACA parameter of the plurality of measured ACA parameters;

calculating an extent of abnormalities with reference to the total number of abnormal angle-locations;

determining a risk of development of the disease of the eye in the patient from a regression model based on the extent of abnormalities;

developing a plan of treatment for the patient based on the determined risk of development of the disease of the eye in the patient; and treating the patient using the plan of treatment, wherein each respective abnormal angle-location is further classified as either closed angle or narrow angle based on one respective ACA parameter of the plurality of measured ACA parameters, and wherein the method further comprises:

dividing the scanned angle-locations of the eye into a plurality of evenly spaced angle-location partitions, wherein each angle-location partition includes one or more adjacent angle-locations;

calculating a partition-specific extent of ACA abnormalities among all angle-locations for each respective angle-location partition, wherein the partition-specific extent of abnormalities is calculated from any of:

(a) total number of angle-locations classified as closed angle;

(b) total number of angle-locations classified as narrow angle; or (c) a combination of (a) and (b); and determining the risk of development of disease of the eye in the patient from a regression model based on the plurality of partition-specific extents of ACA abnormalities.

2. The method of claim 1, wherein the plurality of cross-sectional scan images of the anterior segment is captured using an optical coherence tomography (OCT) instrument.

3. The method of claim 1, wherein the SS position on the cross-sectional scan image of each respective angle-location is located manually by a human grader or automatically by a machine learning model.

4. The method of claim 1, wherein the plurality of measured ACA parameters for each angle-location comprises AOD250, AOD500, TISA250, and TISA500.

5. The method of claim 1, wherein each respective abnormal angle-location is classified as closed angle when the value of the respective ACA parameter is equal to zero.

6. The method of claim 1, wherein each respective abnormal angle-location is classified as narrow angle when the value of the respective ACA parameter is below a respective threshold value for the respective angle-location.

7. The method of claim 6, wherein the respective threshold value for the respective angle-location is determined from a pre-determined cut-off percentile of a normative distribution of the respective ACA parameter measured at the respective angle-location.

8. The method of claim 7, wherein the normative distribution comprises a cross-sectional dataset with measurements collected from a cohort of normal eyes from healthy individuals.

9. The method of claim 7, wherein the normative distribution is specific to an age group corresponding to the patient.

10. The method of claim 7, wherein a first pre-determined cut-off percentile of the normative distribution of the respective ACA parameter at a first respective angle-location is not constrained to be the same as a second pre-determined cut-off percentile of the normative distribution of the respective ACA parameter at a second respective angle-location.

11. The method of claim 1, wherein the extent of abnormalities is calculated from any of:

(a) total number of angle-locations classified as closed angle;

(b) total number of angle-locations classified as narrow angle; or (c) a combination of (a) and (b).

12. The method of claim 1, wherein the regression model comprises either a logistic regression model or a machine learning model and predicts the probability of disease occurrence for determining the risk of development of the disease of the eye in the patient.

13. The method of claim 12, wherein the regression model is a logistic regression model and the probability of disease occurrence is predicted using an odds ratio computed from the regression model based on the extent of ACA abnormalities in the eye.

14. The method of claim 1, wherein the regression model is either a logistic regression model or a machine learning model which predicts the probability of disease occurrence for determining the risk of development of the disease of the eye in the patient and wherein for each respective angle-location partition the respective partition-specific extent of abnormalities is multiplied by a respective weighting factor for the respective partition.

15. The method of claim 14, wherein the regression model is a logistic regression model and the probability of disease occurrence is estimated using an odds ratio computed from the regression model based on the plurality of partition-specific extents of ACA abnormalities in the eye.

16. The method of claim 1, wherein the regression model determines the risk of development of the disease of for the eye in the patient further based on additional information of the patient or the eye comprising:

(a) age;

(b) gender;

(c) anterior chamber depth;

(d) spherical equivalent;

(e) axial length;

(f) pupil diameter; or (g) a combination of any two or more of (a) to (f).

17. A method for analyzing an anterior segment of an eye to estimate the risk of development of a disease of the eye in a patient, the disease of the eye comprising at least one of primary angle closure and primary angle closure glaucoma, the method comprising:

receiving a plurality of cross-sectional scan images of the anterior segment of the eye, wherein each respective image represents a different circumferential angle-location with reference to a central axis of a pupil of the eye, with spaced circumferential separation between respective images across the 360° radial space;

locating a plurality of scleral spur (SS) positions, wherein each respective SS position is located on a respective cross-sectional scan image of a respective angle-location;

measuring a plurality of anterior chamber angle (ACA) parameters for each respective angle-location based on the SS position of the respective angle-location;

classifying each respective angle-location as either normal or abnormal based on one respective ACA parameter of the plurality of measured ACA parameters;

calculating an extent of abnormalities with reference to the total number of abnormal angle-locations;

determining a risk of development of the disease of the eye in the patient from a regression model based on the extent of abnormalities;

developing a plan of treatment for the patient based on the determined risk of development of the disease of the eye in the patient; and treating the patient using the plan of treatment, wherein the SS position on the cross-sectional scan image of each respective angle-location is located manually by a human grader or automatically by a machine learning model, and wherein the machine learning model is a trained deep neural network comprising:

an input module which receives the respective cross-sectional scan image of the respective angle-location;

an output module which informs the pixel coordinates of the located SS position on the respective cross-sectional scan image; and a set of intermediate layers consisting at least one convolutional layer, followed by at least one pooling layer, and further followed by at least one fully connected layer.

18. The method of claim 17, wherein the deep neural network is trained by a supervised learning approach using a plurality of paired input-output examples, each paired input-output example comprising a cross-sectional scan image of an anterior segment as input, and a set of coordinates for ground-truth location of the SS position on the corresponding cross-sectional scan image labelled by one or more human graders as output.

* * * * *